(12) United States Patent
Nageswaran et al.

(10) Patent No.: US 12,042,413 B2
(45) Date of Patent: Jul. 23, 2024

(54) DELIVERY OF MEDICAL DEVICES

(71) Applicant: Covidien LP, Mansfield, MA (US)

(72) Inventors: Ashok Nageswaran, Irvine, CA (US); Gopan Patel, Orange, CA (US)

(73) Assignee: COVIDIEN LP, Mansfield, MA (US)

( * ) Notice: Subject to any disclaimer, the term of this patent is extended or adjusted under 35 U.S.C. 154(b) by 328 days.

(21) Appl. No.: 17/301,560

(22) Filed: Apr. 7, 2021

(65) Prior Publication Data

US 2022/0323246 A1 Oct. 13, 2022

(51) Int. Cl.
*A61F 2/966* (2013.01)
*A61F 2/00* (2006.01)

(52) U.S. Cl.
CPC ...... *A61F 2/966* (2013.01); *A61F 2002/0081* (2013.01); *A61F 2002/9665* (2013.01)

(58) Field of Classification Search
CPC .............. A61F 2/966; A61F 2002/0081; A61F 2002/9665; A61F 2002/823; A61F 2002/9534; A61F 2/962; A61F 2/9662
See application file for complete search history.

(56) References Cited

U.S. PATENT DOCUMENTS

| | | |
|---|---|---|
| 3,416,531 A | 12/1968 | Lowell |
| 4,364,391 A | 12/1982 | Toye |
| 4,425,919 A | 1/1984 | Alston, Jr. et al. |
| 4,516,972 A | 5/1985 | Samson |
| 4,723,936 A | 2/1988 | Buchbinder et al. |
| 4,790,831 A | 12/1988 | Skribiski |
| 4,990,151 A | 2/1991 | Wallsten |
| 5,011,478 A | 4/1991 | Cope |
| 5,026,377 A | 6/1991 | Burton et al. |
| 5,037,404 A | 8/1991 | Gold et al. |
| 5,098,393 A | 3/1992 | Amplatz et al. |
| 5,108,411 A | 4/1992 | Mckenzie |

(Continued)

FOREIGN PATENT DOCUMENTS

| | | |
|---|---|---|
| CA | 2223399 A1 | 12/1996 |
| CA | 2721902 A1 | 12/2009 |

(Continued)

OTHER PUBLICATIONS

Covidien's Pipeline Embolization Device and Delivery System Product Description and Instructions for Use Jun. 2010.

(Continued)

*Primary Examiner* — Todd J Scherbel
(74) *Attorney, Agent, or Firm* — Fortem IP LLP

(57) ABSTRACT

A stent delivery system can include a core member having a distal portion, where the distal portion is configured to be positioned within a lumen of the stent; a cover having a first end portion coupled to the distal portion of the core member and a free second end portion, the cover having (a) a first position in which the second end portion of the cover is configured to at least partially surround a proximal end portion of the stent while the stent is positioned over the core member in a compressed state, and (b) a second position in which the second end portion of the cover is uncoupled from the stent; and a shoulder coupled to the distal portion of the core member at a location distal to the first end portion of the cover, the shoulder configured to abut the proximal end portion of the stent.

20 Claims, 13 Drawing Sheets

(56) References Cited

U.S. PATENT DOCUMENTS

| | | |
|---|---|---|
| 5,147,370 A | 9/1992 | Mcnamara et al. |
| 5,178,158 A | 1/1993 | De Toledo |
| 5,201,316 A | 4/1993 | Pomeranz et al. |
| 5,209,734 A | 5/1993 | Hurley et al. |
| 5,279,562 A | 1/1994 | Sirhan et al. |
| 5,279,596 A | 1/1994 | Castaneda et al. |
| 5,292,311 A | 3/1994 | Cope |
| 5,318,032 A | 6/1994 | Lonsbury et al. |
| 5,318,525 A | 6/1994 | West et al. |
| 5,318,529 A | 6/1994 | Kontos |
| 5,358,493 A | 10/1994 | Schweich, Jr. et al. |
| 5,382,259 A | 1/1995 | Phelps et al. |
| 5,389,087 A | 2/1995 | Miraki |
| 5,403,292 A | 4/1995 | Ju |
| 5,437,288 A | 8/1995 | Schwartz et al. |
| 5,445,646 A | 8/1995 | Euteneuer et al. |
| 5,454,795 A | 10/1995 | Samson |
| 5,458,605 A | 10/1995 | Klemm |
| 5,474,563 A | 12/1995 | Myler et al. |
| 5,478,349 A | 12/1995 | Nicholas |
| 5,484,444 A | 1/1996 | Braunschweiler et al. |
| 5,496,294 A | 3/1996 | Hergenrother et al. |
| 5,499,975 A | 3/1996 | Cope et al. |
| 5,522,822 A | 6/1996 | Phelps et al. |
| 5,531,721 A | 7/1996 | Pepin et al. |
| 5,534,007 A | 7/1996 | St, Germain et al. |
| 5,545,209 A | 8/1996 | Roberts et al. |
| 5,554,139 A | 9/1996 | Okajima |
| 5,569,220 A | 10/1996 | Webster, Jr. |
| 5,571,135 A | 11/1996 | Fraser et al. |
| 5,573,520 A | 11/1996 | Schwartz et al. |
| 5,584,821 A | 12/1996 | Hobbs et al. |
| 5,599,325 A | 2/1997 | Ju et al. |
| 5,599,326 A | 2/1997 | Carter |
| 5,601,539 A | 2/1997 | Corso, Jr. |
| 5,636,641 A | 6/1997 | Fariabi |
| 5,645,559 A | 7/1997 | Hachtman et al. |
| 5,658,264 A | 8/1997 | Samson |
| 5,662,622 A | 9/1997 | Gore et al. |
| 5,676,659 A | 10/1997 | Mcgurk |
| 5,695,483 A | 12/1997 | Samson |
| 5,695,499 A | 12/1997 | Helgerson et al. |
| 5,702,373 A | 12/1997 | Samson |
| 5,702,418 A | 12/1997 | Ravenscroft |
| 5,704,926 A | 1/1998 | Sutton |
| 5,709,703 A | 1/1998 | Lukic et al. |
| 5,711,909 A | 1/1998 | Gore et al. |
| 5,725,513 A | 3/1998 | Ju et al. |
| 5,725,571 A | 3/1998 | Imbert et al. |
| 5,728,063 A | 3/1998 | Preissman et al. |
| 5,741,429 A | 4/1998 | Donadio, III et al. |
| 5,743,876 A | 4/1998 | Swanson |
| 5,759,173 A | 6/1998 | Preissman et al. |
| 5,772,641 A | 6/1998 | Wilson |
| 5,782,811 A | 7/1998 | Samson et al. |
| 5,791,036 A | 8/1998 | Goodin et al. |
| 5,795,341 A | 8/1998 | Samson |
| 5,833,632 A | 11/1998 | Jacobsen et al. |
| 5,836,925 A | 11/1998 | Soltesz |
| 5,836,926 A | 11/1998 | Peterson et al. |
| 5,851,203 A | 12/1998 | Van Muiden |
| 5,853,400 A | 12/1998 | Samson |
| 5,873,866 A | 2/1999 | Kondo et al. |
| 5,876,386 A | 3/1999 | Samson |
| 5,891,112 A | 4/1999 | Samson |
| 5,897,529 A | 4/1999 | Ponzi |
| 5,897,537 A | 4/1999 | Berg et al. |
| 5,902,290 A | 5/1999 | Peacock, III et al. |
| 5,906,605 A | 5/1999 | Coxum |
| 5,935,161 A | 8/1999 | Robinson et al. |
| 5,938,653 A | 8/1999 | Pepin |
| 5,951,494 A | 9/1999 | Wang et al. |
| 5,951,539 A | 9/1999 | Nita et al. |
| 5,961,510 A | 10/1999 | Fugoso et al. |
| 5,968,053 A | 10/1999 | Revelas |
| 5,968,069 A | 10/1999 | Dusbabek et al. |
| 5,971,975 A | 10/1999 | Mills et al. |
| 5,984,963 A | 11/1999 | Ryan et al. |
| 6,017,323 A | 1/2000 | Chee |
| 6,030,371 A | 2/2000 | Pursley |
| 6,045,547 A | 4/2000 | Ren et al. |
| 6,053,903 A | 4/2000 | Samson |
| 6,053,904 A | 4/2000 | Scribner et al. |
| 6,077,258 A | 6/2000 | Lange et al. |
| 6,077,295 A | 6/2000 | Limon et al. |
| 6,077,297 A | 6/2000 | Robinson et al. |
| 6,083,152 A | 7/2000 | Strong |
| 6,093,177 A | 7/2000 | Javier, Jr. et al. |
| 6,105,651 A | 8/2000 | Leanna |
| 6,106,510 A | 8/2000 | Lunn et al. |
| 6,106,540 A | 8/2000 | White et al. |
| 6,123,723 A | 9/2000 | Konya et al. |
| 6,126,685 A | 10/2000 | Lenker et al. |
| 6,135,992 A | 10/2000 | Wang |
| 6,149,680 A | 11/2000 | Shelso et al. |
| 6,152,912 A | 11/2000 | Jansen et al. |
| 6,152,944 A | 11/2000 | Holman et al. |
| 6,159,219 A | 12/2000 | Ren |
| 6,165,163 A | 12/2000 | Chien et al. |
| 6,165,166 A | 12/2000 | Samuelson et al. |
| 6,171,295 B1 | 1/2001 | Garabedian et al. |
| 6,171,296 B1 | 1/2001 | Chow |
| 6,171,297 B1 | 1/2001 | Pedersen et al. |
| 6,186,986 B1 | 2/2001 | Berg et al. |
| 6,193,739 B1 | 2/2001 | Chevillon et al. |
| 6,197,015 B1 | 3/2001 | Wilson |
| 6,217,565 B1 | 4/2001 | Cohen |
| 6,217,566 B1 | 4/2001 | Ju et al. |
| 6,251,132 B1 | 6/2001 | Ravenscroft et al. |
| 6,258,080 B1 | 7/2001 | Samson |
| 6,264,683 B1 | 7/2001 | Stack et al. |
| 6,287,315 B1 | 9/2001 | Wijeratne et al. |
| 6,325,807 B1 | 12/2001 | Que |
| 6,350,278 B1 | 2/2002 | Lenker et al. |
| 6,355,027 B1 | 3/2002 | Le et al. |
| 6,355,060 B1 | 3/2002 | Lenker et al. |
| 6,358,238 B1 | 3/2002 | Sherry |
| 6,358,460 B1 | 3/2002 | Hunt, Jr. et al. |
| 6,368,316 B1 | 4/2002 | Jansen et al. |
| 6,371,953 B1 | 4/2002 | Beyar et al. |
| 6,383,171 B1 | 5/2002 | Gifford et al. |
| 6,387,118 B1 | 5/2002 | Hanson |
| 6,395,008 B1 | 5/2002 | Ellis et al. |
| 6,395,017 B1 | 5/2002 | Dwyer et al. |
| 6,398,791 B1 | 6/2002 | Que et al. |
| 6,419,693 B1 | 7/2002 | Fariabi |
| 6,425,898 B1 | 7/2002 | Wilson et al. |
| 6,428,552 B1 | 8/2002 | Sparks |
| 6,443,971 B1 | 9/2002 | Boylan et al. |
| 6,458,075 B1 | 10/2002 | Sugiyama et al. |
| 6,464,684 B1 | 10/2002 | Galdonik |
| 6,468,298 B1 | 10/2002 | Pelton |
| 6,475,184 B1 | 11/2002 | Wang et al. |
| 6,494,907 B1 | 12/2002 | Bulver |
| 6,508,804 B2 | 1/2003 | Sarge et al. |
| 6,508,805 B1 | 1/2003 | Garabedian et al. |
| 6,508,806 B1 | 1/2003 | Hoste |
| 6,517,547 B1 | 2/2003 | Feeser et al. |
| 6,554,820 B1 | 4/2003 | Wendlandt et al. |
| 6,562,021 B1 | 5/2003 | Derbin et al. |
| 6,562,063 B1 | 5/2003 | Euteneuer et al. |
| 6,576,006 B2 | 6/2003 | Limon et al. |
| 6,582,460 B1 | 6/2003 | Cryer |
| 6,589,227 B2 | 7/2003 | Klint |
| 6,602,271 B2 | 8/2003 | Adams et al. |
| 6,607,551 B1 | 8/2003 | Sullivan et al. |
| 6,622,367 B1 | 9/2003 | Bolduc et al. |
| 6,635,047 B2 | 10/2003 | Forsberg |
| 6,638,245 B2 | 10/2003 | Miller et al. |
| 6,641,564 B1 | 11/2003 | Kraus |
| 6,648,654 B1 | 11/2003 | Hembree et al. |
| 6,648,874 B2 | 11/2003 | Parisi et al. |
| 6,652,508 B2 | 11/2003 | Griffin et al. |
| 6,663,614 B1 | 12/2003 | Carter |

(56) References Cited

U.S. PATENT DOCUMENTS

| | | |
|---|---|---|
| 6,669,719 B2 | 12/2003 | Wallace et al. |
| 6,689,120 B1 | 2/2004 | Gerdts |
| 6,699,274 B2 | 3/2004 | Stinson |
| 6,702,782 B2 | 3/2004 | Miller et al. |
| 6,706,055 B2 | 3/2004 | Douk et al. |
| 6,716,207 B2 | 4/2004 | Farnholtz |
| 6,726,659 B1 | 4/2004 | Stocking et al. |
| 6,764,504 B2 | 7/2004 | Wang et al. |
| 6,808,529 B2 | 10/2004 | Fulkerson |
| 6,815,325 B2 | 11/2004 | Ishii |
| 6,817,995 B1 | 11/2004 | Halpern |
| 6,830,575 B2 | 12/2004 | Stenzel et al. |
| 6,837,890 B1 | 1/2005 | Chludzinski et al. |
| 6,843,802 B1 | 1/2005 | Villalobos et al. |
| 6,858,024 B1 | 2/2005 | Berg et al. |
| 6,866,660 B2 | 3/2005 | Garabedian et al. |
| 6,866,679 B2 | 3/2005 | Kusleika |
| 6,932,837 B2 | 8/2005 | Amplatz et al. |
| 6,939,353 B2 | 9/2005 | Que et al. |
| 6,945,970 B2 | 9/2005 | Pepin |
| 6,960,227 B2 | 11/2005 | Jones et al. |
| 6,989,024 B2 | 1/2006 | Hebert et al. |
| 7,001,369 B2 | 2/2006 | Griffin et al. |
| 7,011,675 B2 | 3/2006 | Hemerick et al. |
| 7,025,758 B2 | 4/2006 | Klint |
| 7,074,236 B2 | 7/2006 | Rabkin et al. |
| 7,104,979 B2 | 9/2006 | Jansen et al. |
| 7,147,656 B2 | 12/2006 | Andreas et al. |
| 7,163,523 B2 | 1/2007 | Devens, Jr. et al. |
| 7,166,088 B2 | 1/2007 | Heuser |
| 7,166,099 B2 | 1/2007 | Devens, Jr. |
| 7,166,100 B2 | 1/2007 | Jordan et al. |
| 7,172,575 B2 | 2/2007 | El-nounou et al. |
| 7,228,878 B2 | 6/2007 | Chen et al. |
| 7,306,624 B2 | 12/2007 | Yodfat et al. |
| 7,323,000 B2 | 1/2008 | Monstdt et al. |
| 7,331,948 B2 | 2/2008 | Skarda |
| 7,357,812 B2 | 4/2008 | Andreas et al. |
| 7,371,248 B2 | 5/2008 | Dapolito et al. |
| 7,402,151 B2 | 7/2008 | Rosenman et al. |
| 7,427,288 B2 | 9/2008 | Sater |
| 7,438,712 B2 | 10/2008 | Chouinard |
| 7,445,684 B2 | 11/2008 | Pursley |
| 7,473,271 B2 | 1/2009 | Gunderson |
| 7,473,272 B2 | 1/2009 | Pryor |
| 7,481,804 B2 | 1/2009 | Devens, Jr. |
| 7,507,229 B2 | 3/2009 | Hewitt et al. |
| 7,524,322 B2 | 4/2009 | Monstadt et al. |
| 7,556,634 B2 | 7/2009 | Lee et al. |
| 7,556,710 B2 | 7/2009 | Leeflang et al. |
| 7,569,046 B2 | 8/2009 | Zhou |
| 7,572,290 B2 | 8/2009 | Yodfat et al. |
| 7,582,079 B2 | 9/2009 | Wendlandt et al. |
| 7,597,830 B2 | 10/2009 | Zhou |
| 7,621,904 B2 | 11/2009 | Mcferran et al. |
| 7,625,337 B2 | 12/2009 | Campbell et al. |
| 7,641,646 B2 | 1/2010 | Kennedy, II |
| 7,651,520 B2 | 1/2010 | Fischell et al. |
| 7,655,031 B2 | 2/2010 | Tenne et al. |
| 7,674,411 B2 | 3/2010 | Berg et al. |
| 7,691,138 B2 | 4/2010 | Stenzel et al. |
| 7,708,704 B2 | 5/2010 | Mitelberg et al. |
| 7,717,953 B2 | 5/2010 | Kaplan et al. |
| 7,758,624 B2 | 7/2010 | Dorn et al. |
| 7,766,820 B2 | 8/2010 | Core |
| 7,766,896 B2 | 8/2010 | Kornkven Volk et al. |
| 7,780,646 B2 | 8/2010 | Farnholtz |
| 7,815,600 B2 | 10/2010 | Al-marashi et al. |
| 7,815,608 B2 | 10/2010 | Schafersman et al. |
| 7,815,628 B2 | 10/2010 | Devens, Jr. |
| 7,828,790 B2 | 11/2010 | Griffin |
| 7,867,267 B2 | 1/2011 | Sullivan et al. |
| 7,879,022 B2 | 2/2011 | Bonnette et al. |
| 7,942,925 B2 | 5/2011 | Yodfat et al. |
| 7,955,370 B2 | 6/2011 | Gunderson |
| 7,981,148 B2 | 7/2011 | Aguilar et al. |
| 7,993,385 B2 | 8/2011 | Levine et al. |
| 8,025,692 B2 | 9/2011 | Feeser |
| 8,034,095 B2 | 10/2011 | Randolph et al. |
| 8,042,720 B2 | 10/2011 | Shifrin et al. |
| 8,048,104 B2 | 11/2011 | Monstadt et al. |
| 8,066,754 B2 | 11/2011 | Malewicz |
| 8,083,791 B2 | 12/2011 | Kaplan et al. |
| 8,088,140 B2 | 1/2012 | Ferrera et al. |
| 8,092,508 B2 | 1/2012 | Leynov et al. |
| 8,109,987 B2 | 2/2012 | Kaplan et al. |
| 8,133,266 B2 | 3/2012 | Thomas et al. |
| 8,147,534 B2 | 4/2012 | Berez et al. |
| 8,159,219 B2 | 4/2012 | Estrada et al. |
| 8,187,314 B2 | 5/2012 | Davis et al. |
| 8,257,432 B2 | 9/2012 | Kaplan et al. |
| 8,298,276 B2 | 10/2012 | Ozawa et al. |
| 8,317,850 B2 | 11/2012 | Kusleika |
| 8,366,763 B2 | 2/2013 | Davis et al. |
| 8,382,818 B2 | 2/2013 | Davis et al. |
| 8,480,701 B2 | 7/2013 | Monstadt |
| 8,579,958 B2 | 11/2013 | Kusleika |
| 8,591,566 B2 | 11/2013 | Newell et al. |
| 8,597,321 B2 | 12/2013 | Monstadt et al. |
| 8,790,387 B2 | 7/2014 | Nguyen et al. |
| 8,968,383 B1 | 3/2015 | Johnson et al. |
| 9,072,624 B2 | 7/2015 | Brown et al. |
| 9,827,126 B2 | 11/2017 | Losordo et al. |
| 11,076,972 B2 | 8/2021 | Nageswaran et al. |
| 2001/0020173 A1 | 9/2001 | Klumb et al. |
| 2001/0027310 A1 | 10/2001 | Parisi et al. |
| 2001/0029362 A1 | 10/2001 | Sirhan et al. |
| 2001/0044591 A1 | 11/2001 | Stevens et al. |
| 2001/0049547 A1 | 12/2001 | Moore |
| 2002/0029046 A1 | 3/2002 | Lorentzen et al. |
| 2002/0049412 A1 | 4/2002 | Madrid et al. |
| 2002/0072789 A1 | 6/2002 | Hackett et al. |
| 2002/0107526 A1 | 8/2002 | Greenberg et al. |
| 2002/0111666 A1 | 8/2002 | Hart et al. |
| 2002/0138128 A1 | 9/2002 | Stiger et al. |
| 2002/0156459 A1 | 10/2002 | Ye et al. |
| 2002/0156460 A1 | 10/2002 | Ye et al. |
| 2002/0165523 A1 | 11/2002 | Chin et al. |
| 2003/0004539 A1 | 1/2003 | Linder et al. |
| 2003/0009208 A1 | 1/2003 | Snyder et al. |
| 2003/0050600 A1 | 3/2003 | Ressemann et al. |
| 2003/0191451 A1 | 10/2003 | Gilmartin |
| 2003/0212410 A1 | 11/2003 | Stenzel et al. |
| 2003/0212430 A1 | 11/2003 | Bose et al. |
| 2004/0024416 A1 | 2/2004 | Yodfat et al. |
| 2004/0059292 A1 | 3/2004 | Hisamatsu et al. |
| 2004/0092879 A1 | 5/2004 | Kraus et al. |
| 2004/0111095 A1 | 6/2004 | Gordon et al. |
| 2004/0143239 A1 | 7/2004 | Zhou et al. |
| 2004/0147903 A1 | 7/2004 | Latini |
| 2004/0158230 A1 | 8/2004 | Hunn et al. |
| 2004/0181174 A2 | 9/2004 | Davis et al. |
| 2004/0193140 A1 | 9/2004 | Griffin et al. |
| 2004/0193243 A1 | 9/2004 | Mangiardi et al. |
| 2004/0220585 A1 | 11/2004 | Nikolchev et al. |
| 2004/0230285 A1 | 11/2004 | Gifford et al. |
| 2004/0260271 A1 | 12/2004 | Huyser et al. |
| 2004/0260384 A1 | 12/2004 | Allen |
| 2005/0033403 A1 | 2/2005 | Ward et al. |
| 2005/0070794 A1 | 3/2005 | Deal et al. |
| 2005/0090802 A1 | 4/2005 | Connors et al. |
| 2005/0096724 A1 | 5/2005 | Stenzel et al. |
| 2005/0119719 A1 | 6/2005 | Wallace et al. |
| 2005/0125051 A1 | 6/2005 | Eidenschink et al. |
| 2005/0131449 A1 | 6/2005 | Salahieh et al. |
| 2005/0143773 A1 | 6/2005 | Abrams et al. |
| 2005/0149160 A1 | 7/2005 | Mcferran |
| 2005/0182388 A1 | 8/2005 | Garabedian et al. |
| 2005/0182475 A1 | 8/2005 | Jen et al. |
| 2005/0228361 A1 | 10/2005 | Tremaglio |
| 2005/0240254 A1 | 10/2005 | Austin |
| 2005/0273149 A1 | 12/2005 | Tran et al. |
| 2005/0277949 A1 | 12/2005 | Que et al. |
| 2006/0030835 A1 | 2/2006 | Sherman et al. |

(56) References Cited

U.S. PATENT DOCUMENTS

| | | |
|---|---|---|
| 2006/0030923 A1 | 2/2006 | Gunderson |
| 2006/0036309 A1 | 2/2006 | Hebert et al. |
| 2006/0058865 A1 | 3/2006 | Case et al. |
| 2006/0064123 A1 | 3/2006 | Bonnette et al. |
| 2006/0074477 A1 | 4/2006 | Berthiaume et al. |
| 2006/0089618 A1 | 4/2006 | Mcferran et al. |
| 2006/0095050 A1 | 5/2006 | Hartley et al. |
| 2006/0100687 A1 | 5/2006 | Fahey et al. |
| 2006/0116750 A1 | 6/2006 | Hebert et al. |
| 2006/0129166 A1 | 6/2006 | Lavelle |
| 2006/0178698 A1 | 8/2006 | Mcintyre et al. |
| 2006/0184226 A1 | 8/2006 | Austin |
| 2006/0212042 A1 | 9/2006 | Lamport et al. |
| 2006/0217682 A1 | 9/2006 | Stivland et al. |
| 2006/0235502 A1 | 10/2006 | Belluche et al. |
| 2006/0271153 A1 | 11/2006 | Garcia et al. |
| 2007/0027520 A1 | 2/2007 | Sherburne |
| 2007/0032744 A1 | 2/2007 | Lupton |
| 2007/0043430 A1 | 2/2007 | Stinson |
| 2007/0049903 A1 | 3/2007 | Jansen et al. |
| 2007/0078504 A1 | 4/2007 | Mialhe |
| 2007/0088323 A1 | 4/2007 | Campbell et al. |
| 2007/0100421 A1 | 5/2007 | Griffin |
| 2007/0117645 A1 | 5/2007 | Nakashima |
| 2007/0129706 A1 | 6/2007 | Katoh et al. |
| 2007/0161956 A1 | 7/2007 | Heuser |
| 2007/0185446 A1 | 8/2007 | Accisano |
| 2007/0203563 A1 | 8/2007 | Hebert et al. |
| 2007/0233224 A1 | 10/2007 | Leynov et al. |
| 2007/0239254 A1 | 10/2007 | Chia et al. |
| 2007/0239261 A1 | 10/2007 | Bose et al. |
| 2007/0250039 A1 | 10/2007 | Lobbins et al. |
| 2007/0250040 A1 | 10/2007 | Provost et al. |
| 2007/0255255 A1 | 11/2007 | Shah et al. |
| 2007/0255388 A1 | 11/2007 | Rudakov et al. |
| 2007/0270779 A1 | 11/2007 | Jacobs et al. |
| 2007/0299424 A1 | 12/2007 | Cumming et al. |
| 2007/0299500 A1 | 12/2007 | Hebert et al. |
| 2007/0299501 A1 | 12/2007 | Hebert et al. |
| 2007/0299502 A1 | 12/2007 | Hebert et al. |
| 2008/0009934 A1 | 1/2008 | Schneider et al. |
| 2008/0015558 A1 | 1/2008 | Harlan |
| 2008/0015678 A1 | 1/2008 | Kaplan et al. |
| 2008/0027528 A1 | 1/2008 | Jagger et al. |
| 2008/0033399 A1 | 2/2008 | Hunn et al. |
| 2008/0033528 A1 | 2/2008 | Satasiya et al. |
| 2008/0051705 A1 | 2/2008 | Von Oepen et al. |
| 2008/0051761 A1 | 2/2008 | Slazas et al. |
| 2008/0071301 A1 | 3/2008 | Matsuura et al. |
| 2008/0077229 A1 | 3/2008 | Andreas et al. |
| 2008/0082083 A1 | 4/2008 | Forde et al. |
| 2008/0091169 A1 | 4/2008 | Heideman et al. |
| 2008/0097398 A1 | 4/2008 | Mitelberg et al. |
| 2008/0108974 A1 | 5/2008 | Yee |
| 2008/0132933 A1 | 6/2008 | Gerber |
| 2008/0140180 A1 | 6/2008 | Dolan et al. |
| 2008/0147001 A1 | 6/2008 | Al-marashi et al. |
| 2008/0147162 A1 | 6/2008 | Andreas et al. |
| 2008/0177249 A1 | 7/2008 | Heuser et al. |
| 2008/0188865 A1 | 8/2008 | Miller et al. |
| 2008/0188928 A1 | 8/2008 | Salahich et al. |
| 2008/0221666 A1 | 9/2008 | Licata et al. |
| 2008/0234660 A2 | 9/2008 | Cumming et al. |
| 2008/0234795 A1 | 9/2008 | Snow et al. |
| 2008/0243225 A1 | 10/2008 | Satasiya et al. |
| 2008/0255541 A1 | 10/2008 | Hoffman et al. |
| 2008/0255653 A1 | 10/2008 | Schkolnik |
| 2008/0255654 A1 | 10/2008 | Hebert et al. |
| 2008/0262471 A1 | 10/2008 | Warnock |
| 2008/0262472 A1 | 10/2008 | Lunn et al. |
| 2008/0262592 A1 | 10/2008 | Jordan et al. |
| 2008/0275426 A1 | 11/2008 | Holman et al. |
| 2008/0300667 A1 | 12/2008 | Hebert et al. |
| 2008/0312639 A1 | 12/2008 | Weber |
| 2009/0012500 A1 | 1/2009 | Murata et al. |
| 2009/0082609 A1 | 3/2009 | Condado |
| 2009/0105802 A1 | 4/2009 | Henry et al. |
| 2009/0125053 A1 | 5/2009 | Ferrera et al. |
| 2009/0132019 A1 | 5/2009 | Duffy et al. |
| 2009/0138066 A1 | 5/2009 | Leopold et al. |
| 2009/0143849 A1 | 6/2009 | Ozawa et al. |
| 2009/0149835 A1 | 6/2009 | Velasco et al. |
| 2009/0157048 A1 | 6/2009 | Sutermeister et al. |
| 2009/0160112 A1 | 6/2009 | Ostrovsky |
| 2009/0171319 A1 | 7/2009 | Guo et al. |
| 2009/0204196 A1 | 8/2009 | Weber |
| 2009/0240235 A1 | 9/2009 | Murata |
| 2009/0247878 A1 | 10/2009 | Tanioka et al. |
| 2009/0264985 A1 | 10/2009 | Bruszewski |
| 2009/0287182 A1 | 11/2009 | Bishop et al. |
| 2009/0287183 A1 | 11/2009 | Bishop et al. |
| 2009/0287187 A1 | 11/2009 | Legaspi et al. |
| 2009/0287292 A1 | 11/2009 | Becking et al. |
| 2009/0299333 A1 | 12/2009 | Wendlandt et al. |
| 2009/0299449 A1 | 12/2009 | Styrc |
| 2009/0318947 A1 | 12/2009 | Garcia et al. |
| 2010/0020354 A1 | 1/2010 | Ito |
| 2010/0036363 A1 | 2/2010 | Watanabe et al. |
| 2010/0049293 A1 | 2/2010 | Zukowski et al. |
| 2010/0049297 A1 | 2/2010 | Dorn |
| 2010/0057184 A1 | 3/2010 | Randolph et al. |
| 2010/0057185 A1 | 3/2010 | Melsheimer et al. |
| 2010/0069852 A1 | 3/2010 | Kelley |
| 2010/0087913 A1 | 4/2010 | Rabkin et al. |
| 2010/0094258 A1 | 4/2010 | Shimogami et al. |
| 2010/0094394 A1 | 4/2010 | Beach et al. |
| 2010/0094395 A1 | 4/2010 | Kellett |
| 2010/0100106 A1 | 4/2010 | Ferrera |
| 2010/0160863 A1 | 6/2010 | Heuser |
| 2010/0198334 A1 | 8/2010 | Yodfat et al. |
| 2010/0204770 A1 | 8/2010 | Mas et al. |
| 2010/0217235 A1 | 8/2010 | Thorstenson et al. |
| 2010/0256602 A1 | 10/2010 | Lippert et al. |
| 2010/0256603 A1 | 10/2010 | Lippert et al. |
| 2010/0262157 A1 | 10/2010 | Silver et al. |
| 2010/0268243 A1 | 10/2010 | Parker |
| 2010/0268328 A1 | 10/2010 | Stiger |
| 2010/0274270 A1 | 10/2010 | Patel et al. |
| 2010/0298931 A1 | 11/2010 | Quadri et al. |
| 2010/0331951 A1 | 12/2010 | Bei et al. |
| 2011/0009943 A1 | 1/2011 | Paul et al. |
| 2011/0022157 A1 | 1/2011 | Essinger et al. |
| 2011/0029065 A1 | 2/2011 | Wood et al. |
| 2011/0034987 A1 | 2/2011 | Kennedy |
| 2011/0054586 A1 | 3/2011 | Mayberry et al. |
| 2011/0093055 A1 | 4/2011 | Kujawski |
| 2011/0098804 A1 | 4/2011 | Yeung et al. |
| 2011/0106235 A1 | 5/2011 | Haverkost et al. |
| 2011/0112623 A1 | 5/2011 | Schatz |
| 2011/0147080 A1 | 6/2011 | Slininger et al. |
| 2011/0152760 A1 | 6/2011 | Parker |
| 2011/0160763 A1 | 6/2011 | Ferrera et al. |
| 2011/0178588 A1 | 7/2011 | Haselby |
| 2011/0190862 A1 | 8/2011 | Bashiri et al. |
| 2011/0190865 A1 | 8/2011 | Mchugo et al. |
| 2011/0208292 A1 | 8/2011 | Von Oepen et al. |
| 2011/0224650 A1 | 9/2011 | Itou et al. |
| 2011/0288626 A1 | 11/2011 | Straubinger et al. |
| 2011/0319904 A1 | 12/2011 | Hollett et al. |
| 2012/0029607 A1 | 2/2012 | Mchugo et al. |
| 2012/0035700 A1 | 2/2012 | Leanna et al. |
| 2012/0053681 A1 | 3/2012 | Alkhatib et al. |
| 2012/0059449 A1 | 3/2012 | Dorn et al. |
| 2012/0065660 A1 | 3/2012 | Ferrera et al. |
| 2012/0116494 A1 | 5/2012 | Leynov et al. |
| 2012/0123511 A1 | 5/2012 | Brown |
| 2012/0136350 A1 | 5/2012 | Goshgarian et al. |
| 2012/0253447 A1 | 10/2012 | Hayasaka et al. |
| 2012/0316638 A1 | 12/2012 | Grad et al. |
| 2013/0085562 A1 | 4/2013 | Rincon et al. |
| 2013/0131775 A1 | 5/2013 | Hadley et al. |
| 2013/0172925 A1 | 7/2013 | Garcia et al. |
| 2013/0172979 A1 | 7/2013 | Fargahi |
| 2013/0226276 A1 | 8/2013 | Newell et al. |

(56) References Cited

U.S. PATENT DOCUMENTS

| | | |
|---|---|---|
| 2013/0226278 A1 | 8/2013 | Newell et al. |
| 2013/0261730 A1 | 10/2013 | Bose et al. |
| 2013/0274618 A1 | 10/2013 | Hou et al. |
| 2013/0274859 A1 | 10/2013 | Argentine |
| 2013/0282099 A1 | 10/2013 | Huynh |
| 2013/0289693 A1 | 10/2013 | Maggard et al. |
| 2013/0304185 A1 | 11/2013 | Newell et al. |
| 2014/0025150 A1 | 1/2014 | Lim |
| 2014/0031918 A1 | 1/2014 | Newell et al. |
| 2014/0148893 A1 | 5/2014 | Kusleika |
| 2014/0171826 A1 | 6/2014 | Lampropoulos et al. |
| 2014/0194919 A1 | 7/2014 | Losordo et al. |
| 2014/0200648 A1 | 7/2014 | Newell et al. |
| 2014/0257452 A1* | 9/2014 | Slazas .................. A61F 2/966 623/1.11 |
| 2015/0032198 A1 | 1/2015 | Folk |
| 2015/0066128 A1 | 3/2015 | Losordo et al. |
| 2015/0066129 A1 | 3/2015 | Nageswaran et al. |
| 2015/0066130 A1 | 3/2015 | Haggstrom et al. |
| 2015/0066131 A1 | 3/2015 | Luong et al. |
| 2015/0080937 A1 | 3/2015 | Davidson |
| 2015/0133990 A1 | 5/2015 | Davidson |
| 2015/0164666 A1 | 6/2015 | Johnson et al. |
| 2015/0238336 A1 | 8/2015 | Johnson et al. |
| 2015/0265444 A1 | 9/2015 | Kitaoka |
| 2016/0113795 A1 | 4/2016 | Frid et al. |
| 2017/0035592 A1 | 2/2017 | Haggstrom et al. |
| 2021/0386570 A1 | 12/2021 | Haggstrom et al. |

FOREIGN PATENT DOCUMENTS

| | | |
|---|---|---|
| EP | 0450221 A1 | 10/1991 |
| EP | 1656963 A1 | 5/2006 |
| GB | 1449622 A | 9/1976 |
| GB | 2179258 A | 3/1987 |
| JP | H09503945 A | 4/1997 |
| JP | 3272716 B2 | 4/2002 |
| JP | 2003504127 A | 2/2003 |
| JP | 2005110721 A | 4/2005 |
| JP | 2006021039 A | 1/2006 |
| JP | 2007325639 A | 12/2007 |
| WO | WO 9601591 A1 | 1/1996 |
| WO | WO 0149212 A1 | 7/2001 |
| WO | WO 2010008571 A1 | 1/2010 |
| WO | WO 2010027485 A1 | 3/2010 |
| WO | WO 2010086320 A1 | 8/2010 |
| WO | WO 2010123831 A1 | 10/2010 |
| WO | WO 2011076408 A1 | 6/2011 |
| WO | WO 2011095966 A1 | 8/2011 |
| WO | WO 2012040240 A1 | 3/2012 |
| WO | WO 2012158152 A1 | 11/2012 |

OTHER PUBLICATIONS

DuPont Product and Properties Handbook Teflon FRP Jan. 1998 accessed Jun. 14, 2016 from http:lwww.rjchase.com/ep_handbook.pdf.

International Search Report and Written Opinion dated Jun. 13, 2016; International Application No. PCT/US2016/020382; 12 pages.

International Search Report and Written Opinion from PCT/US2014/050270 dated Nov. 18, 2014.

Jankowitz et al. "Measurement of Intracranial Arteries using Digital Subtraction Angiography with an Internal Control in 85 Patients" University of Pittsburgh Medical Center 2009.

Kim et al. "Sum of the Curve Indices for Estimating the Vascular Tortuousness of the Internal Carotid Arte," Neurointervention 2009; 4: 101-106.

Misumi Properties and Characteristics—Polyurethane—Tensile Strength http://us.misumiec.com/maker/misumi/mech/ roduct/ur/detail.html accessed Apr. 19, 2016.

Osborn "Diagnostic Cerebral Angiography 2nd Edition" 1999 Lippincott Williams & Wilkins pp. 3-38 31 57-81 83-116 135-151 173-194.

Plastics International Hardness Scale—Durometer Comparisons of Materials 2016 accessed Jun. 14, 2016 from http:/www.plasticsintl.com/polyhardness.htm.

Sugawara et al. "Carotid-Femoral Pulse Wave Velocity: Impact of Different Arterial Path Length Measurements" Artery Res Mar. 2010 4 (1) : 27-31.

Thermal tech Equipment Shore Durometer Conversion Chart accessed Jun. 14, 2016 from http:/www.ttequip/knowledgelibraryfTechPage ShoreDurometerConversionChart.htm.

Wikipedia Polyether block amide—Tensile Strength https://en.wikipedia.org/wiki/polyether_block_amide accessed Apr. 19, 2016.

WS Hampshire Inc. Typical Properties of PTFE—Tensile Strength http://catalog.wshamshire.com/asset/psg_teflon_ptfe.pdf accessed Apr. 19, 2016.

* cited by examiner

DELIVERY OF MEDICAL DEVICES

BACKGROUND

Walls of the vasculature, particularly arterial walls, may develop areas of pathological dilatation called aneurysms. As is well known, aneurysms have thin, weak walls that are prone to rupturing. Aneurysms can be the result of the vessel wall being weakened by disease, injury, or a congenital abnormality. Aneurysms could be found in different parts of the body, and the most common are abdominal aortic aneurysms and brain or cerebral aneurysms in the neurovasculature. When the weakened wall of an aneurysm ruptures, it can result in death, especially if it is a cerebral aneurysm that ruptures.

Aneurysms are generally treated by excluding the weakened part of the vessel from the arterial circulation. For treating a cerebral aneurysm, such reinforcement is done in many ways including: (i) surgical clipping, where a metal clip is secured around the base of the aneurysm; (ii) packing the aneurysm with small, flexible wire coils (micro-coils); (iii) using embolic materials to "fill" an aneurysm; (iv) using detachable balloons or coils to occlude the parent vessel that supplies the aneurysm; and (v) intravascular stenting.

Intravascular stents are well known in the medical arts for the treatment of vascular stenoses or aneurysms. Stents are prostheses that expand radially or otherwise within a vessel or lumen to provide support against the collapse of the vessel. Methods for delivering these intravascular stents are also well known.

In conventional methods of introducing a compressed stent into a vessel and positioning it within in an area of stenosis or an aneurysm, a guiding catheter having a distal tip is percutaneously introduced into the vascular system of a patient. The guiding catheter is advanced within the vessel until its distal tip is proximate the stenosis or aneurysm. A guidewire positioned within an inner lumen of a second, inner catheter and the inner catheter are advanced through the distal end of the guiding catheter. The guidewire is then advanced out of the distal end of the guiding catheter into the vessel until the distal portion of the guidewire carrying the compressed stent is positioned at the point of the lesion within the vessel. Once the compressed stent is located at the lesion, the stent may be released and expanded so that it supports the vessel.

SUMMARY

At least one aspect of the disclosure provides methods and apparatuses for delivering an occluding device or devices (e.g., stent or stents) in the body. The occluding device can easily conform to the shape of the tortuous vessels of the vasculature. The occluding device can be used in a variety of applications. For example, in some embodiments, the occluding device can direct the blood flow within a vessel away from an aneurysm. Additionally, such an occluding device can allow adequate blood flow to be provided to adjacent structures such that those structures, whether they are branch vessels or oxygen demanding tissues, are not deprived of the necessary blood flow.

The delivery of an intravascular stent to a treatment site within the vessel of a patient requires substantial precision. Generally, during the implantation process, a stent is passed through a vessel to a treatment location. The stent can be expanded at the treatment location, often by allowing a first end of the stent to expand and thereafter slowly expanding the remainder of the stent until the entire stent has been expanded. The process of initially contacting the vessel wall as the first end of the stent expands can be referred to as "landing" the stent. The final position of the stent within the vessel is generally determined by its initial placement or landing within the vessel. In some situations, the stent may initially be "landed" in a suboptimal location within the vessel. Using traditional methods and apparatuses, it may be very difficult for a clinician to reposition the stent within the vessel. For example, a clinician may be unable to recapture, collapse, withdraw, or resheath the stent back into the catheter after the stent has been partially expanded within the vessel. As such, the initial landing is critical to successful placement of the stent.

The subject technology is illustrated, for example, according to various aspects described below. Various examples of aspects of the subject technology are described as numbered embodiments (1, 2, 3, etc.) for convenience. These are provided as examples and do not limit the subject technology. It is noted that any of the dependent embodiments may be combined in any combination with each other or one or more other independent embodiments, to form an independent embodiment. The other embodiments can be presented in a similar manner. The following is a non-limiting summary of some embodiments presented herein:

Embodiment 1. A system for delivering a stent to a patient's vasculature via a catheter, the system comprising:
  a core member having a distal portion, wherein the distal portion is configured to be positioned within a lumen of the stent;
  a cover having a first end portion coupled to the distal portion of the core member and a free second end portion, the cover moveable between a first position and a second position; and
  a shoulder coupled to the distal portion of the core member at a location distal to the first end portion of the cover, the shoulder configured to abut a proximal end portion of the stent when the stent is in a compressed state and positioned over the core member within the catheter,
  wherein,
    when at least a portion of the stent is positioned in the compressed state within the catheter, the cover is in the first position in which the second end portion of the cover is interposed radially between a proximal end region of the stent and an inner surface of the catheter, and
    when the catheter is proximal of the first end portion of the cover, the cover is in the second position.

Embodiment 2. The system of Embodiment 1, wherein, when the cover is in the first position, the cover is interposed radially between (a) a length of the system within the catheter spanning a distal end region of the shoulder to the proximal end region of the stent, and (b) the inner surface of the catheter.

Embodiment 3. The system of Embodiment 1 or Embodiment 2, wherein the cover comprises one or more longitudinal strips.

Embodiment 4. The system of Embodiment 3, wherein the one or more longitudinal strips are configured to wrap around the proximal end portion of the stent when the cover is in the first position.

Embodiment 5. The system of any of the Embodiments 1-4, wherein the stent comprises an expanded state, and wherein the cover transitions from the first position to the second position in response to the stent transitioning from the compressed state to the expanded state.

Embodiment 6. The system of any of the Embodiments 1-5, wherein the cover at least partially surrounds the shoulder.

Embodiment 7. The system of any of the Embodiments 1-6, wherein the shoulder has a distal face configured to push the stent distally.

Embodiment 8. The system of any of the Embodiments 1-7, wherein the shoulder is spaced apart from the first end of the cover.

Embodiment 9. The system of any of the Embodiments 1-8, wherein a length of the cover is less than an outer diameter of the stent.

Embodiment 10. The system of any of the Embodiments 1-9, wherein a length of the cover is less than half of an outer diameter of the stent.

Embodiment 11. The system of any of the Embodiments 1-10, wherein the cover is a first cover, the system further comprising a second cover, the second cover having a first end coupled to the distal segment of the core member and a second end configured to at least partially surround a distal end of the stent.

Embodiment 12. A system for delivering a stent to a patient's vasculature, the system comprising:
  a catheter;
  a manipulation member having a distal region and configured to be slidably received within a lumen of the catheter;
  a cover having a first portion coupled to the distal region of the manipulation member and a free second portion, the cover having (a) a first position in which the second portion is configured to at least partially surround a proximal portion of a stent while the stent is compressed within the catheter, and (b) a second position in which the second portion is decoupled from the stent; and
  a shoulder member coupled to the distal region of the manipulation member, the shoulder member configured to abut a proximal terminus of the stent when the stent is compressed within the catheter.

Embodiment 13. The system of Embodiment 12, wherein, when the cover is in the first position, the cover is interposed radially between (a) a length of the system within the catheter spanning a distal end region of the shoulder to a proximal terminus of the stent, and (b) an inner surface of the catheter.

Embodiment 14. The system of Embodiment 12 or 13, wherein the cover comprises one or more longitudinal strips.

Embodiment 15. The system of Embodiment 14, wherein the one or more longitudinal strips are configured to wrap around the proximal portion of the stent when the cover is in the first position.

Embodiment 16. The system of any of the Embodiments 12-15, wherein the stent comprises an expanded state, and wherein the cover transitions from the first position to the second position in response to the stent transitioning from the compressed state to the expanded state.

Embodiment 17. The system of any of the Embodiments 12-16, wherein the cover at least partially surrounds the shoulder member.

Embodiment 18. The system any of the Embodiments 12-17, wherein the shoulder member has a distal face configured to push the stent distally.

Embodiment 19. The system any of the Embodiments 12-18, wherein the shoulder member is spaced apart from the first portion of the cover.

Embodiment 20. The system any of the Embodiments 12-19, wherein a length of the cover is less than an outer diameter of the stent.

Embodiment 21. The system any of the Embodiments 12-20, wherein a length of the cover is less than half of an outer diameter of the stent.

Embodiment 22. The system of any of the Embodiments 12-21, wherein the cover is a first cover, the stent delivery system further comprising a second cover, the second cover having a first portion coupled to the distal region of the manipulation member and a second portion configured to at least partially surround a distal end of the stent.

Embodiment 23. A method of delivering a treatment device to a treatment site within a patient's vasculature, the method comprising:
  positioning a treatment device within a blood vessel lumen at a treatment site, the treatment device comprising:
    a catheter defining a lumen therethrough;
    a core member slidably disposed within the catheter lumen;
    a stent in a compressed state positioned within the catheter lumen; and
    a cover having a first end portion coupled to the core member and a free second end portion, wherein the second end portion is positioned radially between the stent and an inner surface of the catheter;
  releasing the stent from the catheter such that the stent self-expands into apposition with the blood vessel wall, and
  in response to expansion of the stent, decoupling the cover from the stent such that at least a portion of the cover is not radially between the stent and the catheter.

Embodiment 24. The method of Embodiment 23, wherein the cover is movable between a first position and a second position, and wherein the cover transitions from the first position to the second position in response to the expansion of the stent.

Embodiment 25. The method of any of the Embodiments 23 or 24, wherein the treatment device further comprises a shoulder coupled to the distal portion of the core member at a location distal to the first end portion of the cover, the shoulder configured to abut the proximal end portion of the stent when the stent is in a compressed state and positioned over the core member within the catheter.

Embodiment 26. The method of Embodiment 25, wherein, when the cover is positioned radially between the stent and an inner surface of the catheter, the cover is interposed radially between (a) a length of the device within the catheter spanning a distal end region of the shoulder to a proximal end region of the stent, and (b) the inner surface of the catheter.

Embodiment 27. The method of any of the Embodiments 23-26, wherein the cover comprises one or more longitudinal strips.

Embodiment 28. The method of Embodiment 27, wherein the one or more longitudinal strips are configured to wrap around a proximal portion of the stent when the cover is positioned radially between the stent and an inner surface of the catheter.

Embodiment 29. The method of any of the Embodiments 23-28, wherein the treatment site is an aneurysm.

Embodiment 30. A device for delivering a stent to a patient's vasculature via a catheter, the device comprising:
  a core member having a distal portion, wherein the distal portion is configured to be positioned within a lumen of the stent;

a cover having (a) a first end portion coupled to the distal portion of the core member and having a radial position that is substantially fixed relative to the core member, and (b) a second end portion configured to move radially relative to the core member, and a shoulder coupled to the distal portion of the core member at a location distal to the first end portion of the cover, the shoulder positioned proximally adjacent a proximal end portion of the stent when the stent is in a compressed state and positioned over the core member within the catheter, wherein the cover is moveable between a first position and a second position such that:

when at least a portion of the stent is positioned in the compressed state within the catheter, the cover is in the first position in which the second end portion of the cover is distal of a proximal terminus of the stent, and when the catheter is proximal of the first end portion of the cover, the cover is in the second position in which the second end portion is proximal of a proximal terminus of the stent.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

DETAILED DESCRIPTION

Figure 1:
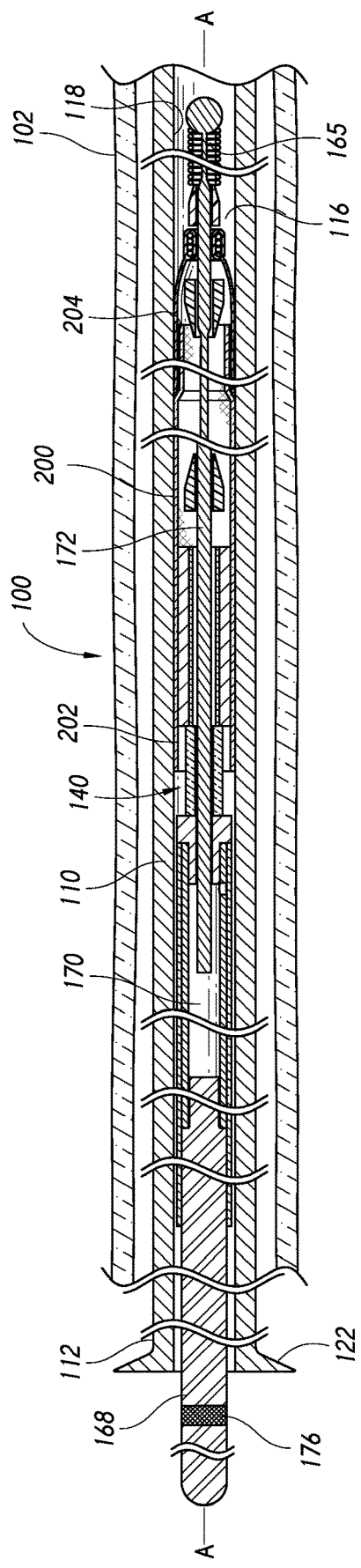
FIG. 1 is a side, cross-sectional view of a medical device delivery system disposed within a body lumen, according to some embodiments.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

FIGS. 1-8 depict embodiments of a medical device delivery system 100 which may be used to deliver and/or deploy a medical device, such as but not limited to a stent 200, into a hollow anatomical structure such as a blood vessel 102. The stent 200 can comprise a proximal end 202 and a distal end 204. The stent 200 can comprise a braided stent or other form of stent such as a laser-cut stent, roll-up stent, etc. The stent 200 can optionally be configured to act as a "flow diverter" device for treatment of aneurysms, such as those found in blood vessels including arteries in the brain or within the cranium, or in other locations in the body such as peripheral arteries. The stent 200 can optionally be similar to any of the versions or sizes of the PIPELINE™ Embolization Device marketed by Covidien of Mansfield, Massachusetts USA. The stent 200 can further alternatively comprise any suitable tubular medical device and/or other features, as described herein.

Figure 2:
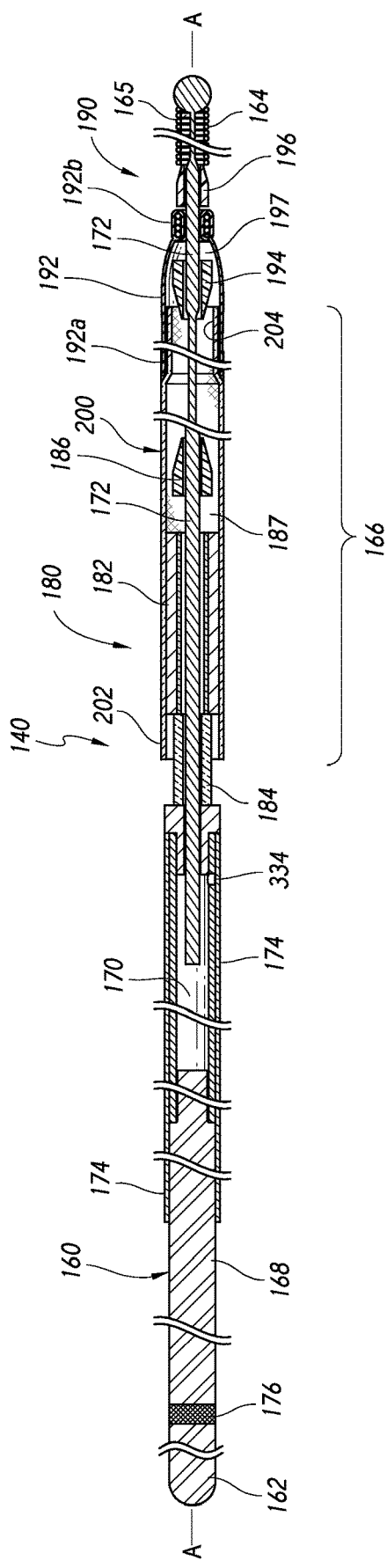
FIG. 2 is a side, cross-sectional view of a core assembly of the medical device delivery system shown in FIG. 1, according to some embodiments.

As shown in FIG. 1, the depicted medical device delivery system 100 can comprise an elongate tube or catheter 110 which slidably receives a core assembly 140 configured to carry the stent 200 through the catheter 110. FIG. 2 illustrates the core assembly 140 without depicting the catheter 110 for clarity. The depicted catheter 110 (see FIGS. 1, 3-8) has a proximal end 112 and an opposing distal end 114 which can be positioned at a treatment site within a patient, an internal lumen 116 extending from the proximal end 112 to the distal end 114, and an inner surface 118 facing the lumen 116. At the distal end 114, the catheter 110 has a distal opening 120 through which the core assembly 140 may be advanced beyond the distal end 114 in order to expand or deploy the stent 200 within the blood vessel 102. The proximal end 112 may include a catheter hub 122. The catheter 110 can define a generally longitudinal axis A-A extending between the proximal end 112 and the distal end 114. When the delivery system 100 is in use, the longitudinal axis need not be straight along some or any of its length.

The catheter 110 can optionally comprise a microcatheter. For example, the catheter 110 can optionally comprise any of the various lengths of the MARKSMAN™ catheter available from Covidien of Mansfield, Massachusetts USA. The catheter 110 can optionally comprise a microcatheter having an inner diameter of about 0.030 inches or less, and/or an outer diameter of 3 French or less near the distal end 114. Instead of or in addition to these specifications, the catheter 110 can comprise a microcatheter which is configured to percutaneously access the internal carotid artery, or a location within the neurovasculature distal of the internal carotid artery, with its distal opening 120.

Information regarding additional embodiments of the catheter 110, and additional details and components that can optionally be used or implemented in the embodiments of the catheter described herein, can be found in U.S. Patent Application Publication No. US 2011/0238041 A1, published on Sep. 29, 2011, titled Variable Flexibility Catheter. The entirety of the aforementioned publication is hereby incorporated by reference herein and made a part of this specification.

The core assembly 140 can comprise a core member 160 configured to extend generally longitudinally through the lumen 116 of the catheter 110. The core member 160 can have a proximal end or section 162 and a terminal or distal end 164, which can include a tip coil 165. The core member 160 can also comprise an intermediate portion 166 located between the proximal end 162 and the distal end 164, which intermediate portion is the portion of the core member 160 onto or over which the stent 200 is positioned or fitted or extends when the core assembly 140 is in the pre-deployment configuration as shown in FIGS. 1-5.

The core member 160 can generally comprise any member(s) with sufficient flexibility, column strength and thinness to move the stent 200 or other medical device through the catheter 110. The core member 160 can therefore comprise a wire, or a tube such as a hypotube, or a braid, coil, or other suitable member(s), or a combination of wire(s), tube(s), braid(s), coil(s), etc. The embodiment of the core member 160 depicted in FIGS. 1-8 is of multi-member construction, comprising a proximal wire 168, a tube 170 (e.g., a hypotube) connected at its proximal end to a distal end of the proximal wire 168, and a distal wire 172 connected at its proximal end to a distal end of the tube 170. In some embodiments, the proximal wire 168 can extend continuously through the entire length of the tube 170 and then form the distal wire 172, for example, as an integral unit with the proximal wire 168. In some such embodiments, the outer diameter of the portion of the wire extending through the tube 170 can be less than an inner diameter of the tube 170, leaving an annular gap between the outer surface of the wire and the inner surface of the tube. An outer layer 174, which can comprise a layer of lubricious material such as PTFE (polytetrafluoroethylene or TEFLON™) or other lubricious polymers, can cover some or all of the tube 170 and/or proximal wire 168. The proximal and/or distal wires 168, 172 may taper or vary in diameter along some or all of their lengths. The proximal wire 168 may include one or more fluorosafe markers 176, and such marker(s) can be located on a portion of the wire 168 that is not covered by the outer layer 174, e.g., proximal of the outer layer 174. This portion of the wire 168 marked by the marker(s) 176, and/or proximal of any outer layer 174, can comprise a bare metal outer surface.

The core assembly 140 can further comprise a proximal device interface 180 and/or a distal device interface 190 that can interconnect the medical device or stent 200 with the core member 160. The proximal device interface 180 can comprise a proximal engagement member 182 that is configured to underlie the stent 200 and engage an inner wall of the stent. In this manner, the proximal engagement member 182 cooperates with the overlying inner wall 118 of the catheter 110 to grip the stent 200 such that the proximal engagement member 182 can move the stent 200 along and within the catheter 110, e.g., as the user pushes the core member 160 distally and/or pulls the core member proximally relative to the catheter 110, resulting in a corresponding distal and/or proximal movement of the stent 200 within the catheter lumen 116. In some embodiments, the core assembly 140 and/or the proximal device interface 180 do not include the proximal engagement member 182 of FIGS. 1-8, as described herein.

The proximal engagement member 182 can be fixed to the core member 160 (e.g., to the distal wire 172 thereof in the depicted embodiment) so as to be immovable relative to the core member 160, either in a longitudinal/sliding manner or a radial/rotational manner. Alternatively, as depicted in FIGS. 1-8, the proximal engagement member 182 can be coupled to (e.g., mounted on) the core member 160 so that the proximal engagement member 182 can rotate about the longitudinal axis A-A of the core member 160 (e.g., of the distal wire 172), and/or move or slide longitudinally along the core member. In such embodiments, the proximal engagement member 182 can have an inner lumen that receives the core member 160 therein such that the proximal engagement member 182 can slide and/or rotate relative to the core member 160. Additionally, in such embodiments, the proximal device interface 180 can further comprise a proximal restraint 184 that is fixed to the core member 160 and located proximal of the proximal engagement member 182, and/or a distal restraint 186 that is fixed to the core member 160 and located distal of the proximal engagement member 182. The proximal and distal restraints 184, 186 can be spaced apart along the core member 160 by a longitudinal distance that is greater than the length of the proximal engagement member, so as to leave one or more longitudinal gaps 187 between the proximal engagement member 182 and one or both of the proximal and distal restraints 184, 186, depending on the position of the proximal engagement member between the restraints. When present, the longitudinal gap(s) 187 allow the proximal engagement member 182 to slide longitudinally along the core member 160 between the restraints 184, 186. The longitudinal range of motion of the proximal engagement member 182 between the restraints 184, 186 is approximately equal to the total length of the longitudinal gap(s) 187.

Instead of or in addition to the longitudinal gap(s) 187, the proximal device interface 180 can comprise a radial gap 188 (FIG. 3) between the outer surface of the core member 160 and the inner surface of the proximal engagement member 182. Such a radial gap 188 can be formed when the proximal engagement member 182 is constructed with an inner luminal diameter that is somewhat larger than the outer diameter of the corresponding portion of the core member 160. When present, the radial gap 188 allows the proximal engagement member 182 to rotate about the longitudinal axis A-A of the core member 160 between the restraints 184, 186. The presence of longitudinal gaps 187 of at least a minimal size on either side of the proximal engagement member 182 can also facilitate the rotatability of the proximal engagement member.

One or both of the proximal and distal restraints 184, 186 can have an outside diameter or other radially outermost dimension that is smaller than the outside diameter or other radially outermost dimension of the proximal engagement member 182, so that one or both of the restraints 184, 186 will tend not to contact the inner surface of the stent 200 during operation of the core assembly 140.

In the proximal device interface 180 shown in FIGS. 1-8, the stent 200 can be moved distally or proximally within the catheter 100 via the proximal engagement member 182. During distal movement, the distal end of the proximal restraint 184 bears on the proximal end of the engagement member 182, and the engagement member urges the stent 200 distally via frictional engagement with the inner surface of the stent 200 (assisted by the overlying catheter 110). During proximal movement, the proximal end of the distal restraint 186 bears on the distal end of the engagement member 182, which in turn moves the stent 200 proximally via such frictional engagement. Proximal movement of the stent 200 relative to the catheter 110 can be employed when withdrawing or re-sheathing the stent 200 back into the distal end 114 of the catheter 110, as will be discussed in greater detail below. When the stent 200 has been partially deployed and a portion of the stent remains disposed between the proximal engagement member 182 and the inner wall of the catheter (see FIGS. 6, 7), the stent 200 can be withdrawn back into the distal opening 120 of the catheter by moving the core assembly 140 (including the engagement member 182) proximally relative to the catheter 110 (and/or moving the catheter 110 distally relative to the core assembly 140). Re-sheathing in this manner remains possible until the engagement member 182 and/or catheter 110 have been moved to a point where the engagement member 182 is beyond the distal opening 120 of the catheter 110 and the stent 200 is released from between the member 182 and the catheter 110.

Optionally, the proximal edge of the proximal engagement member 182 can be positioned just distal of the proximal edge of the stent 200 when in the delivery configuration shown in FIGS. 1-5. In some such embodiments, this enables the stent 200 to be re-sheathed when as little as about 3 mm of the stent remains in the catheter 110. Therefore, with stents 200 of typical length, resheathability of 75% or more can be provided (i.e. the stent 200 can be re-sheathed when 75% or more of it has been deployed).

The distal device interface 190 can comprise a distal engagement member 192 that can take the form of, for example, a distal device cover or distal stent cover (generically, a "distal cover"). The distal cover 192 can be configured to reduce friction between the medical device or stent 200 (e.g., the distal portion or distal end thereof) and the inner surface 118 of the catheter 110. For example, the distal cover 192 can be configured as a lubricious, flexible structure having a free first end or section 192*a* that can extend over at least a portion of the stent 200 and/or intermediate portion 166 of the core assembly 160, and a fixed second end or section 192*b* that can be coupled (directly or indirectly) to the core member 160.

The distal cover 192 can have a first or delivery position, configuration, or orientation (see, e.g., FIGS. 1-5) in which the distal cover can extend proximally relative to the distal tip 164, or proximally from the second section 192*b* or its (direct or indirect) attachment to the core member 160, and at least partially surround or cover a distal portion of the stent 200. The distal cover 192 can be movable from the first or delivery orientation to a second or resheathing position, configuration, or orientation (see, e.g., FIGS. 7-8) in which the distal cover can be everted such that the first end 192*a* of the distal cover is positioned distally relative to the second end 192*b* of the distal cover 192 to enable the resheathing of the core assembly 140, either with the stent 200 carried thereby, or without the stent.

The distal cover 192, particularly the first end 192*a* thereof, can comprise one or more flexible, generally longitudinally extending strips, wings, or elongate portions that are coupled to or integrally formed with the second end 192*b*. The distal cover 192 can be manufactured or otherwise cut from a tube of the material selected for the distal cover or from multiple radial portions of such a tube. In such embodiments the first section 192*a* may be formed as multiple longitudinal strips cut from the tube, and the second section 192*b* may be an uncut (or similarly cut) length of the tube. Accordingly, the second section 192*b* and the proximally extending strips of the first section 192*a* may form a single, integral device or structure. In some embodiments, the distal cover 192 comprises only one, or no more than two strips, wings, or elongate portions.

In some embodiments, the distal cover 192 may comprise a tube or a longitudinally slit tube, and the first section 192*a* can include two or more semi-cylindrical or partially cylindrical strips or tube portions separated by a corresponding number of generally parallel, longitudinally oriented cuts or separations formed or otherwise positioned in the sidewall of the tube. Therefore, when in the pre-expansion state, as shown in FIGS. 1-5, the first section 192*a* may generally have the shape of a longitudinally split or longitudinally slotted tube extending or interposed radially between the outer surface of the stent or device 200 and the inner surface 118 of the catheter 110.

In various embodiments, the strips, wings, or elongate portions of the first section 192*a* may collectively span substantially the entire circumference of the outer surface of the stent 200 (e.g., where the cuts between the strips are splits of substantially zero width) or be sized somewhat less than the entire circumference (e.g., where the cuts between the strips are slots having a nonzero width). In accordance with some embodiments, the width of the strips, wings, or elongate portions of the first section 192*a* can be between about 0.5 mm and about 4 mm. The width can be about 0.5 mm to about 1.5 mm. In accordance with some embodiments, the width can be about 1 mm.

The strips, wings, or elongate portions of the first section 192*a* can also extend longitudinally over at least a portion of the distal portion of the stent 200. In various embodiments, the first section 192*a* can extend between about 1 mm and about 3 mm, or between about 1.5 mm and about 2.5 mm, or about 2 mm, over the distal portion of the stent.

The first section 192*a* and the second section 192*b* can define a total length of the distal cover 192. In some embodiments, the total length can be between about 4 mm and about 10 mm. The total length can also be between about 5.5 mm and about 8.5 mm. In some embodiments, the total length can be about 7 mm.

The strips of the first section 192*a* may be of substantially uniform size. For example, the first section 192*a* can comprise two strips spanning approximately 180 degrees each, three strips spanning approximately 120 degrees each, four strips spanning approximately 90 degrees each, or otherwise be divided to collectively cover all or part of the circumference of the stent, etc. Alternatively, the strips may differ in angular sizing and coverage area without departing from the scope of the disclosure. In one embodiment, only two strips or tube portions are employed in the first section 192*a*. The use of only two strips can facilitate radial expansion, distal movement and/or fold-over or everting of the first section 192*a*, as discussed herein, while minimizing the number of free or uncontained strips in the blood vessel lumen and any potential for injuring the vessel by virtue of contact between a strip and the vessel wall.

The distal cover 192 can be manufactured using a lubricious and/or hydrophilic material such as PTFE or Teflon®, but may be made from other suitable lubricious materials or lubricious polymers. The distal cover can also comprise a radiopaque material which can be blended into the main material (e.g., PTFE) to impart radiopacity. The distal cover 192 can have a thickness of between about 0.0005" and about 0.003". In some embodiments, the distal cover can be one or more strips of PTFE having a thickness of about 0.001".

The distal cover 192 (e.g., the second end 192b thereof) can be fixed to the core member 160 (e.g., to the distal wire 172 or distal tip 164 thereof) so as to be immovable relative to the core member 160, either in a longitudinal/sliding manner or a radial/rotational manner. Alternatively, as depicted in FIGS. 1-3 and 5-8, the distal cover 192 (e.g., the second end 192b thereof) can be coupled to (e.g., mounted on) the core member 160 so that the distal cover 192 can rotate about the longitudinal axis A-A of the core member 160 (e.g., of the distal wire 172), and/or move or slide longitudinally along the core member. In such embodiments, the second end 192b can have an inner lumen that receives the core member 160 therein such that the distal cover 192 can slide and/or rotate relative to the core member 160. Additionally in such embodiments, the distal device interface 190 can further comprise a proximal restraint 194 that is fixed to the core member 160 and located proximal of the (second end 192b of the) distal cover 192, and/or a distal restraint 196 that is fixed to the core member 160 and located distal of the (second end 192b of the) distal cover 192. The proximal and distal restraints 194, 196 can be spaced apart along the core member 160 by a longitudinal distance that is greater than the length of the second end 192b, so as to leave one or more longitudinal gaps 197 between the second end 192b and one or both of the proximal and distal restraints 194, 196, depending on the position of the second end 192b between the restraints. When present, the longitudinal gap(s) 197 allow the second end 192b and/or distal cover 192 to slide longitudinally along the core member 160 between the restraints 194, 196. The longitudinal range of motion of the second end 192b and/or distal cover 192 between the restraints 194, 196 is approximately equal to the total length of the longitudinal gap(s) 197.

Instead of or in addition to the longitudinal gap(s) 197, the distal device interface 190 can comprise a radial gap 198 between the outer surface of the core member 160 (e.g., of the distal wire 172) and the inner surface of the second end 192b. Such a radial gap 198 can be formed when the second end 192b is constructed with an inner luminal diameter that is somewhat larger than the outer diameter of the corresponding portion of the core member 160. When present, the radial gap 198 allows the distal cover 192 and/or second end 192b to rotate about the longitudinal axis A-A of the core member 160 between the restraints 194, 196. The presence of longitudinal gaps 197 of at least a minimal size on either side of the second end 192b can also facilitate the rotatability of the distal cover.

One or both of the proximal and distal restraints 194, 196 can have an outside diameter or other radially outermost dimension that is smaller than the (e.g., pre-deployment) outside diameter or other radially outermost dimension of the distal cover 192, so that one or both of the restraints 194, 196 will tend not to bear against or contact the inner surface 118 of the catheter 110 during operation of the core assembly 140.

In the embodiment depicted in FIGS. 1-3 and 5-8, the second end 192b of the distal cover 192 includes an internal hoop 192c which can comprise a (metallic or polymeric) coil as depicted, or other generally rigid, tubular or cylindrical internal member such as a short segment of relatively stiff polymeric or metallic tubing. The internal hoop 192c can be contained in an annular enclosure or loop(s) formed by the second end 192b, or otherwise attached to or integrated into the second end 192b in a manner that tends to maintain an inside diameter of the distal cover 192 in the second end 192b that is larger than the outside diameter of the adjacent portion of the core member 160 (or the wire 172 thereof). In other words, the hoop 192c can help maintain the presence of the radial gap 198 between the inside diameter of the second end 192b and the outside diameter of the core member 160 or distal wire 172.

The annular enclosure or loop(s) of the second end 192b can be formed by wrapping a portion of a sheet or tube of the distal cover material (e.g., PTFE) around the sidewall and through the lumen of the hoop 192c and adhering, gluing or heat bonding an end of the wrapped portion of the sheet or tube to the adjacent, proximally extending portion of the sheet or tube. Thus are formed two layers that are adhered together on the proximal side of the hoop 192. Where the distal cover material comprises PTFE, unsintered PTFE can be used to enable bonding the two portions of the material together with heat and pressure, which is not typically possible with "ordinary" or sintered PTFE.

In operation, the distal cover 192, and in particular the first section 192a, can generally cover and protect the distal end 204 of the stent 200 as the stent 200 is moved distally within the catheter 110. The distal cover 192 may serve as a bearing or buffer layer that, for example, inhibits filament ends of the distal end 204 of the stent 200 (where the stent 200 comprises a braided stent) from contacting the inner surface 118 of the catheter 110, which could damage the stent 200 and/or catheter 110, or otherwise compromise the structural integrity of the stent 200. Since the distal cover 192 may be made of a lubricious material, the distal cover 192 may exhibit a low coefficient of friction that allows the distal end 204 of the stent 200 to slide axially within the catheter 110 with relative ease. The coefficient of friction between the distal cover and the inner surface of the catheter can be between about 0.02 and about 0.4. For example, in embodiments in which the distal cover and the catheter are formed from PTFE, the coefficient of friction can be about 0.04. Such embodiments can advantageously improve the ability of the core assembly to pass through the catheter, especially in tortuous vasculature.

Further, as shown in FIGS. 1-5, at least a portion of the distal cover 192 can at least partially extend or be interposed radially between the distal portion of the stent 200 and the inner surface 118 of the catheter 110 in the first position, configuration, or orientation. In the first orientation, the first section 192a of the distal cover 192 can extend from the second section 192b in a proximal direction to a point where the first section is interposed between the distal portion of the stent 200 and the inner surface 118 of the catheter 110. In this orientation, the first section of the distal cover can take on a "proximally oriented" position or configuration.

Figure 4:
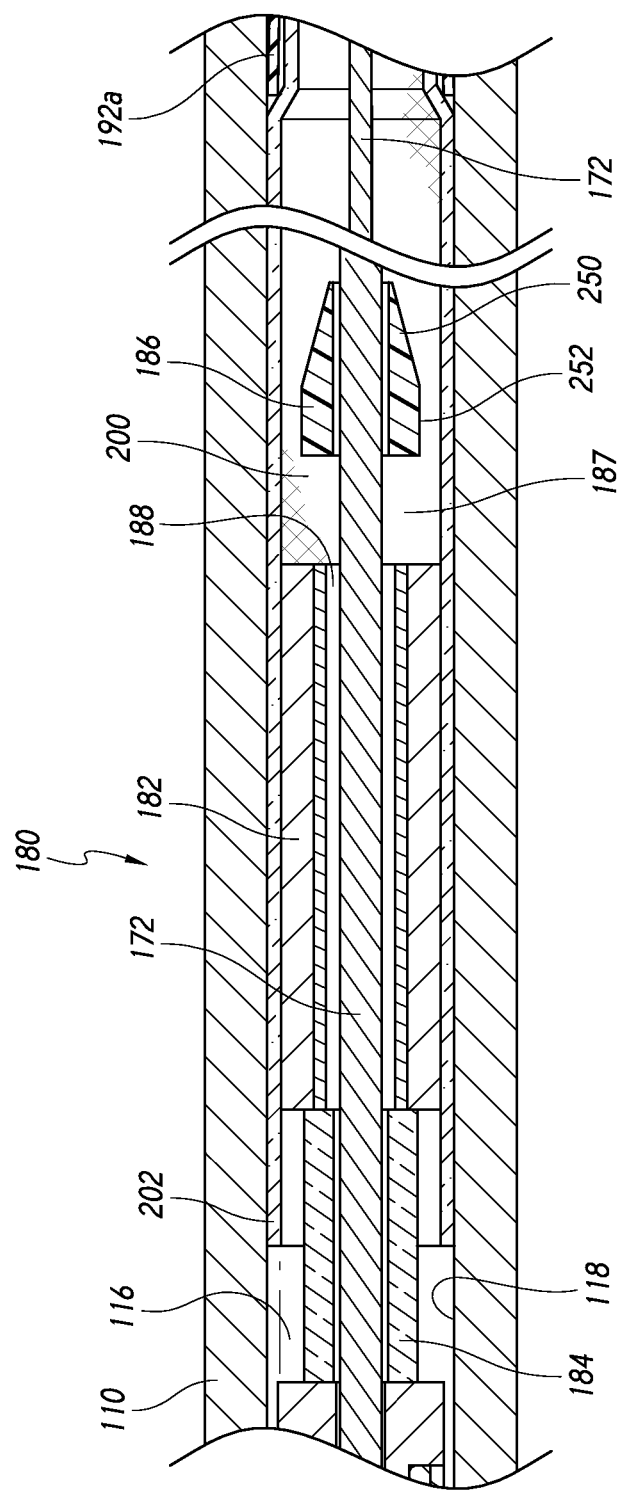
FIG. 4 is another enlarged side, cross-sectional view of the delivery system shown in FIG. 1.
Figure 5:
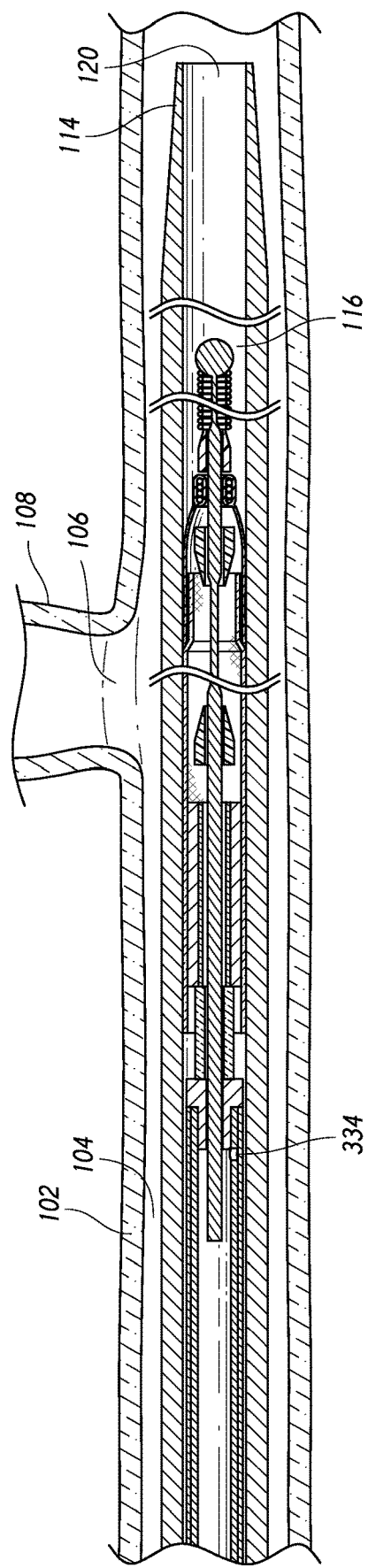
FIG. 5 is a side, cross-sectional view of a medical device delivery system in a first position, adjacent to a target location, according to some embodiments.
Figure 6:
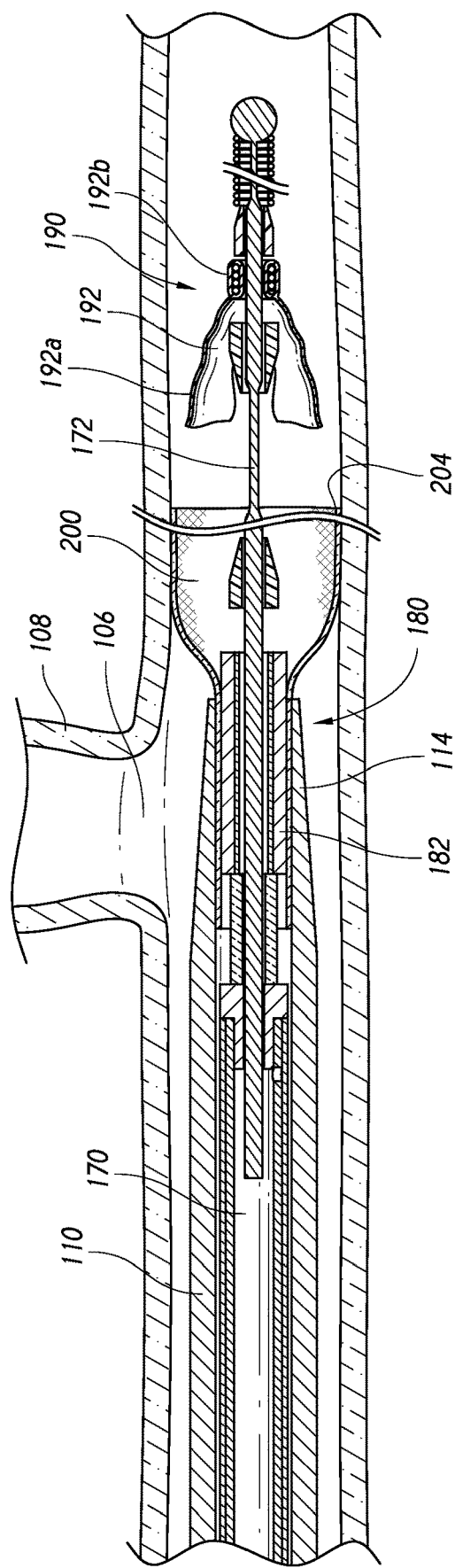
FIG. 6 is a side, cross-sectional view of the delivery system shown in FIG. 5, wherein the system is in a second position in which a stent thereof is partially expanded and a distal cover is disengaged from the stent, according to some embodiments.

The core assembly 140 shown in FIGS. 1-4 can operate as illustrated in FIGS. 5-9. The core assembly 140 can be distally advanced until the distal portion of the stent 200 is positioned distally beyond the distal end 114 of the catheter 110 to permit expansion of the distal portion of the stent 200 into a lumen 104 of the blood vessel 102. As the distal portion of the stent 200 expands, it can cause the distal cover 192 to be opened or moved from the first orientation. Because (when braided) the stent 200 can often foreshorten as it expands, the stent 200 can withdraw from engagement with the distal cover 192, as shown in FIG. 6.

Figure 7:
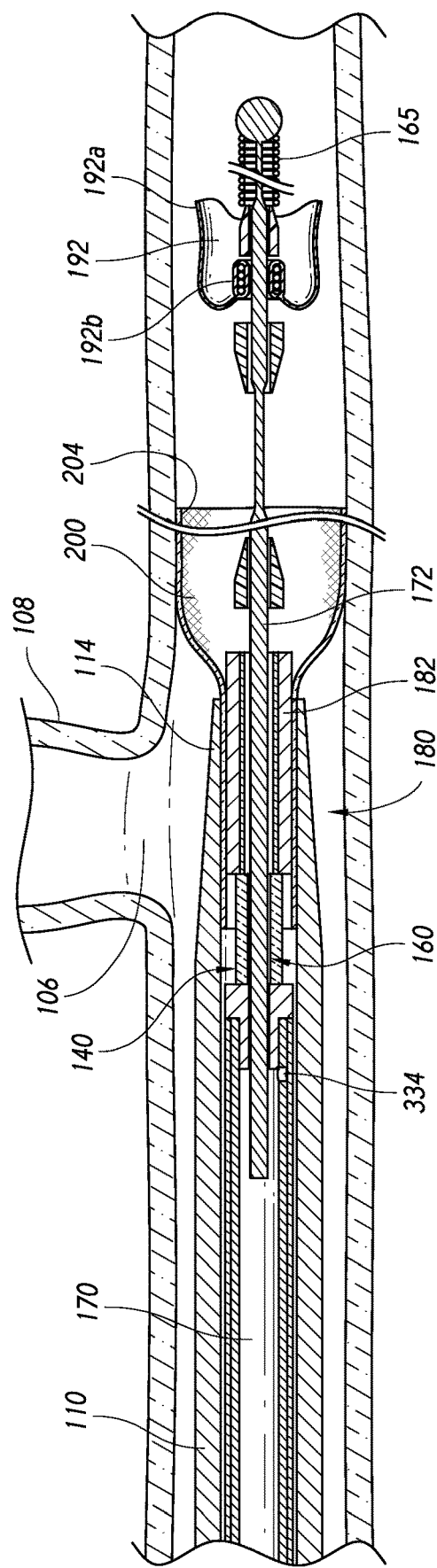
FIG. 7 is a side, cross-sectional view of the delivery system shown in FIG. 5, wherein the distal cover is moved to an everted position, according to some embodiments.
Figure 8:
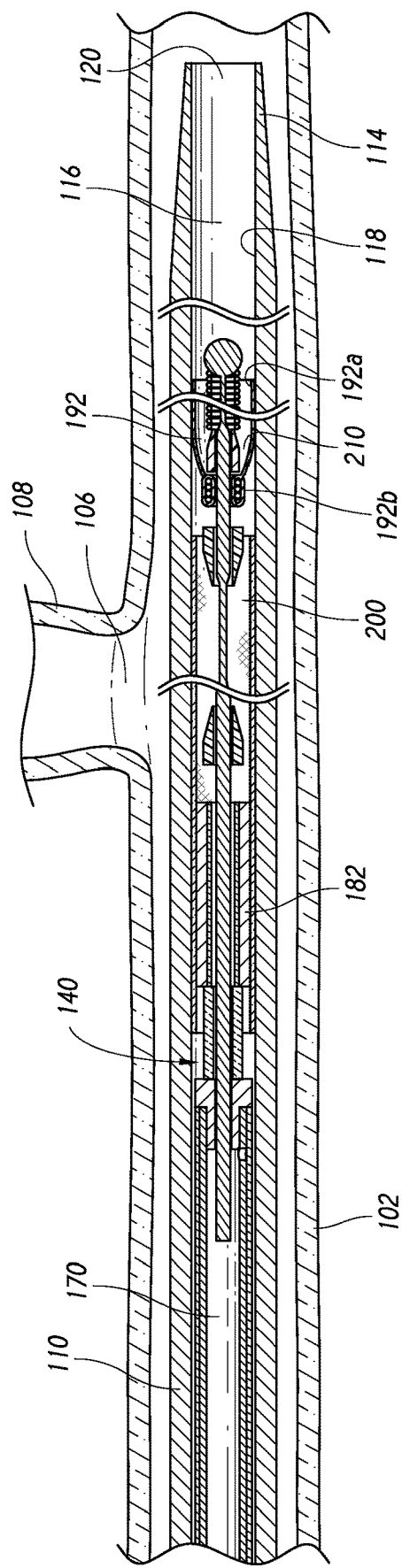
FIG. 8 is a side, cross-sectional view of the delivery system shown in FIG. 5, wherein the stent has been retracted into a catheter of the system, according to some embodiments.

After the distal cover 192 has become disengaged from the stent 200 to reach the state shown in FIG. 6, the cover can proceed to the second orientation as shown in FIG. 7, as oncoming blood flow and/or other forces urge the first section 192a distally relative to the core member 160. Alternatively, the distal cover 192 can remain substantially in the disengaged, proximally-extending configuration shown in FIG. 6 until the core assembly 140 is withdrawn proximally into the catheter 110, at which point the distal end 114 of the catheter 110 can force the approaching first section 192a of the cover 192 to evert or otherwise take on the second configuration as shown in FIGS. 7-8. In each case, the distal cover 192 can move toward an everted position or configuration in which the first section 192a of the distal cover 192 is flipped, everted or rotated to extend in a distal direction or in a "distally oriented" position or configuration. In some embodiments of a distally-oriented second configuration, all or at least a portion of the first section 192a is located distal of all or at least a portion of the second section 192b.

Figure 9:
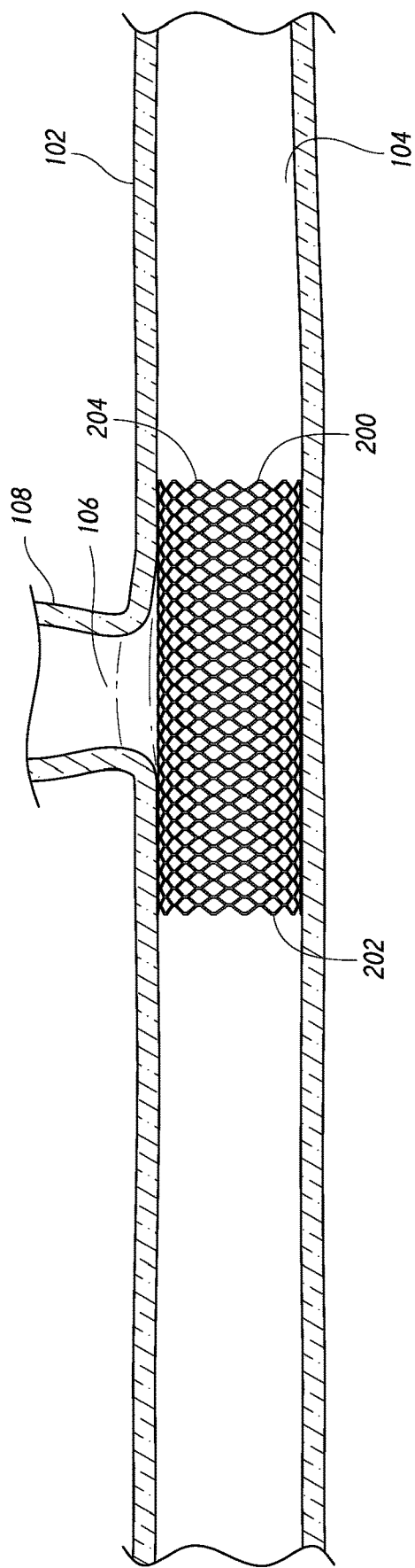
FIG. 9 is a side, cross-sectional view of the stent expanded at the target location, according to some embodiments.

The stent 200 can be further unsheathed and subsequently released into position in the lumen 104 of the vessel 102, e.g., across and/or spanning a neck 106 of an aneurysm 108 formed in the wall of the vessel 102 (as shown in FIG. 9), or the stent 200 can be retracted and withdrawn back into the catheter 110 (as shown in FIG. 8), if needed. In either situation, when the distal portion of the core assembly 140 is withdrawn into the lumen 116 of the catheter 110, the distal cover 192 can be retracted into the catheter 110 in the second position, configuration, or orientation, in which the distal cover 192 can be at least partially everted, as shown in FIGS. 7 and 8. This can facilitate complete resheathing of the stent 200 and/or the core assembly 140 within the catheter 110.

Figure 3:
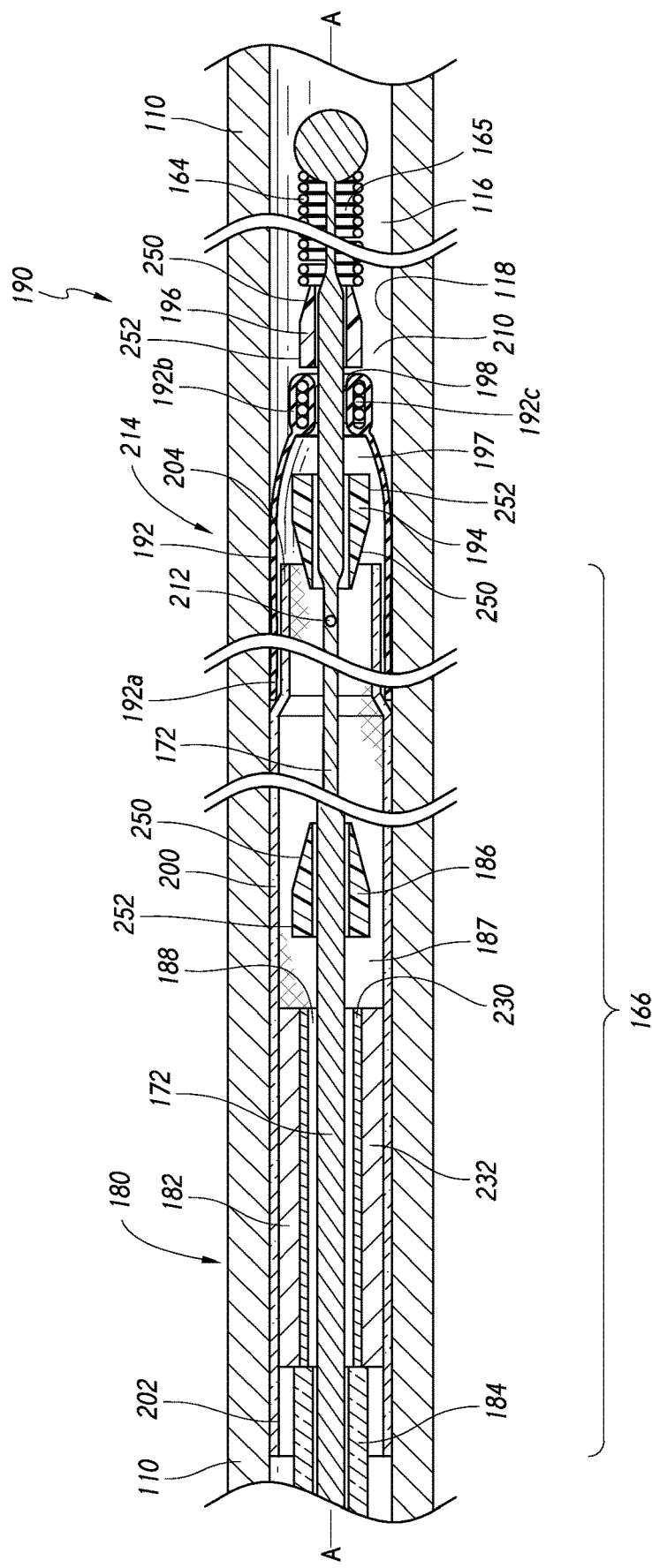
FIG. 3 is an enlarged side, cross-sectional view of the delivery system shown in FIG. 1.

In some embodiments, in the first orientation, the first section 192a of the distal cover 192 is positioned outside of a radial space 210 located between the core assembly 160 or axis A-A (in either case distal of the second section 192b or the location where the distal cover 192 is connected to the core member) and the inner wall of the catheter 110, as shown in FIG. 3. The distal cover 192 can extend proximally from the second section 192b and/or connection location, and away from the radial space 210. Additionally, in some such embodiments, in the second orientation, some or all of the first section 192a of the distal cover 192 can extend distally through the radial space 210 upon retraction of the core assembly 140 into the catheter 110, as shown in FIG. 8.

Further, in some embodiments, the first section 192a of the distal cover 192 can radially overlap with the distal end 204 of the stent 200 at an overlap point 212 along the core member 160. As illustrated in FIG. 3, the overlap point 212 can be located along the core member 160 at or near a distal end 214 of the intermediate portion 166 of the core member 160, or at any location along the core member 160 that underlies an overlap of the (first section 192a of the) distal cover 192 over the stent 200 when the core assembly 140 is in its pre-deployment configuration shown in FIGS. 1-3 and 5. Additionally, in some such embodiments, in the second orientation, the first section 192a of the distal cover 192 no longer overlaps with the (distal end 204 of) the stent 200 at the overlap point 212 (and the first section 192a can be located distally of such location), upon retraction of the core assembly 140 into the catheter 110, as shown in FIG. 8.

In the second orientation, as shown in FIGS. 7-8, there is no longer radial overlap of the stent 200 and the cover 192 at the overlap point 212 or at the distal end 214 of the intermediate section 166. Thus, after disengagement of the distal cover 192 from the stent 200, the core assembly 140 can be proximally withdrawn into the catheter 110 and the distal cover 192 can generally extend in a distal direction away from the overlap point 212. As also shown in FIG. 8, at such time that the stent 200 is resheathed or withdrawn into the catheter 110 after partial expansion or deployment, the stent 200 and the distal cover 192 will not overlap at the overlap point 212. Thus, the distal cover 192 will not overlap the stent 200 or the overlap point 212 after at least partial expansion of the stent 200 when the core assembly 140 is withdrawn into the catheter 110. Further, once the distal cover 192 is disengaged, the intermediate portion 166 of the core member 160 can be positioned radially adjacent to the distal end 114 of the catheter 110 with the distal cover 192 being positioned outside of the radial space between the intermediate portion 166 and the (inner wall 118 of the) catheter 110. Accordingly, the movement and configuration of the distal cover 192 can enable the core assembly 140 to provide radial clearance between the core member 160 or the intermediate portion 166 and the catheter 110 for facilitating resheathing of the core member 160 and stent 200, as shown in FIGS. 7-8.

Structures other than the herein-described embodiments of the distal cover 192 may be used in the core assembly 140 and/or distal device interface 190 to cover or otherwise interface with the distal end 204 of the stent 200. For example, a protective coil or other sleeve having a longitudinally oriented, proximally open lumen may be employed. Suitable such protective coils include those disclosed in U.S. Patent Application Publication No. 2009/0318947 A1, published on Dec. 24, 2009, titled SYSTEM AND METHOD FOR DELIVERING AND DEPLOYING AN OCCLUDING DEVICE WITHIN A VESSEL.

In embodiments of the core assembly 140 that employ both a rotatable proximal engagement member 182 and a rotatable distal cover 192, the stent 200 can be rotatable with respect to the core member 160 about the longitudinal axis A-A thereof, by virtue of the rotatable (connections of the) proximal engagement member 182 and distal cover 192. In such embodiments, the stent 200, proximal engagement member 182 and distal cover 192 can rotate together in this manner about the core member. When the stent 200 can rotate about the core member 160, the core assembly 140 can be advanced more easily through tortuous vessels as the tendency of the vessels to twist the stent and/or core assembly is negated by the rotation of the stent, proximal engagement member and distal cover about the core member. In addition, the required push force or delivery force is reduced, as the user's input push force is not diverted into torsion of the stent and/or core member. The tendency of a twisted stent and/or core member to untwist suddenly or "whip" upon exiting tortuosity or deployment of the stent, and the tendency of a twisted stent to resist expansion upon deployment, are also reduced or eliminated. Further, in some such embodiments of the core assembly 140, the user can "steer" the core assembly 140 via the tip coil 165, particularly if the coil 165 is bent at an angle in its unstressed configuration. Such a coil tip can be rotated about the axis A-A relative to the stent 200, engagement member 182 and/or distal cover 192 by rotating the distal end 162 of the core member 160. Thus the user can point the coil tip in the desired direction of travel of the core assembly, and upon advancement of the core assembly the tip will guide the core assembly in the chosen direction.

As noted, embodiments of the distal cover can provide various advantages. For example, the use of the distal cover can allow the core assembly to be easily urged toward the treatment site within the catheter. This can advantageously reduce the delivery force required to move the core assembly through the catheter. Further, a flexible distal cover such as the depicted distal cover 192 can also allow the distal portion of the stent to open or expand radially immediately as the distal portion of the stent exits the catheter. The distal cover can be easily urged away from the first or encapsulating position or configuration such that the expansion of the stent is not hindered and expansion can be predictable to the clinician. Where employed, this can be a significant improvement over prior art devices that used a relatively rigid tube, such as a coil to distally restrain a distal end of the stent, which could impede or make unpredictable the proper expansion or deployment of the distal end of the stent.

Further, where the first portion 192a is flexible, evertible, and/or provides a minimal cross-section, the intermediate portion of the core assembly can be easily recaptured within the catheter (with or without the stent coupled thereto (e.g., mounted thereon)) to facilitate resheathing. Thus, the catheter can remain in place in the vasculature and the entire core assembly can be withdrawn therefrom. This can enable the clinician to "telescope" one or more other stents (e.g., delivering more than one stent such that it overlaps with another stent) without having to remove the catheter, saving time and reducing trauma to the patient. This also enables the clinician to remove the core assembly and stent entirely from the catheter in the event of a failure to deploy or other evident defect in the stent, and insert another core assembly and stent through the same catheter, with the same time savings and reduction in trauma.

In other embodiments, the distal device interface 190 can omit the distal cover 192, or the distal cover can be replaced with a component similar to the proximal engagement member 182. Where the distal cover 192 is employed, it can be connected to the distal tip coil 165, e.g., by being wrapped around and enclosing some or all of the winds of the coil 165, or being adhered to or coupled to the outer surface of the coil by an adhesive or a surrounding shrink tube. In still other embodiments, the distal device interface 190 (or the proximal device interface 180) can be omitted altogether.

Additional details regarding the proximal engagement member will now be discussed, with reference especially to FIGS. 3, 10 and 11. Some embodiments of the proximal engagement member 182 can be of multi-layer construction, which can be useful for facilitating rotation of the engagement member 182 and/or stent 200 about the core member 160. For example, the proximal engagement member 182 can comprise a generally tubular or cylindrical inner layer 230, and another generally tubular or cylindrical outer layer 232 that overlies the inner layer 230. The outer layer 232 can be adhered to or otherwise securely joined to the inner layer 230 so that the two cannot rotate or move longitudinally relative to each other during the ordinary use of the core assembly 140 and delivery system 100.

The inner layer 230 and outer layer 232 can differ in mechanical properties such as hardness. For example, the outer layer 232 can comprise a relatively soft material to facilitate relatively high-friction or "high-grip" contact with the inner surface of the stent 200. The inner layer can be formed from a relatively hard or stiff material to facilitate low-friction engagement with the adjacent portion of the core member 160, and high hoop strength to resist inward deflection or collapse of the inner lumen 234 of the proximal engagement member 182. Such inward deflection or collapse can result in "pinching" the core member 160 with the inner layer 230 and consequent degradation of the ability of the proximal engagement member 182 to rotate and/or move longitudinally with respect to the core member 160. When contact does occur between the inner surface of the inner layer 230 and the outer surface of the core member 160, the relatively hard/stiff material of the inner layer 230 minimizes the friction resulting from such contact.

In some embodiments of the multi-layer proximal engagement member, the outer layer 232 can be formed from a relatively soft polymer or elastomer such as silicone, rubber (e.g., Chronoprene™), thermoplastic polyurethane (e.g., Tecoflex™) or polyether block amide (e.g., Pebax™). Whether made of such materials, or of other materials, the outer layer 232 can have a durometer of between 10 A and 50 A, or between 15 A and 40 A, or about 20 A, or about 25 A.

Instead of or in addition to the above-recited materials and/or properties of the outer layer 232, in some embodiments, the inner layer 230 can be formed from polyimide, e.g., a polyimide tube; alternatively a tubular metallic coil (e.g., a stainless steel coil) could be employed, or a metal tube, either with or without slots or a spiral cut formed in the sidewall. Whether made of such materials, or of other materials, the inner layer 230 can have a higher durometer than the outer layer 232, e.g., above 70 D or between 70 D and 100 D.

In some embodiments, the inner and outer layers 230, 232 can be integrally formed. For example, both layers could be formed from a single cylinder of soft material wherein the harder/stiffer inner layer comprises the radially inner portions of the cylinder which have been treated or processed to become harder/stiffer. Or the reverse could be done, wherein a cylinder of hard material is processed to make its outer layer softer and/or higher-friction.

Although, as disclosed above, the outer layer 232 can be made from a variety of materials, silicone is particularly preferred because it offers a high coefficient of friction, high heat resistance to facilitate sterilization, and high creep resistance to resist being "imprinted" with, or interlocked with, the filament or strut pattern of the adjacent medical device or stent 200. The high coefficient of friction of silicone also facilitates the use of a relatively short proximal engagement member, e.g., (for delivery of a neurovascular stent) less than 5 mm, less than 3 mm, between 1 mm and 3 mm, or between 2 mm and 2.5 mm. It is also preferred to use a silicone outer layer 232 in combination with a thermoset material (such as polyimide) for the inner layer 230, of a higher durometer than the outer layer 232, or generally to use thermoset materials for both the inner and outer layers 230, 232, with the outer layer of lower durometer than the inner layer.

Despite these advantages of silicone, it is difficult to process in a manner useful to form a multi-layer tubular component like the proximal engagement member 182, e.g., via co-extrusion. Because of this difficulty, it was necessary for the inventors to develop a method of manufacturing the proximal engagement member 182 with a silicone outer layer 232 and an inner layer of higher-durometer thermoset material such as polyimide.

In one embodiment, the proximal engagement member 182 can be manufactured as follows. A length of polyimide tubing of approximately 100 mm in length can be placed over a metallic mandrel so that the mandrel passes through the lumen of the tubing. The mandrel is sized to fit closely within the tubing lumen so as to hold the tubing in place on the mandrel via frictional engagement with the inner wall of the tubing. In addition, the close fit of the mandrel helps to seal the tubing lumen from inflow of silicone material during the subsequent dip coating of the tubing. Once the tubing is on the mandrel, the mandrel is mounted on a dipping fixture.

A silicone reservoir is provided in the form of a vertical, open-topped cylinder, and the cylinder is prepared by wiping the inner surfaces of it with 70% isopropyl alcohol and allowing it to dry for 5 minutes. The mounted polyimide tubing is prepared in a similar manner by wiping it twice with a lint-free cloth wetted with 70% isopropyl alcohol and allowing it to dry for 5 minutes. Once the tubing is dry, it is "painted" with a primer (e.g., MED-163 Primer from NuSil Technology of Carpinteria, California USA) by first wetting the bristles of an applicator brush with a pipette full of the primer, and then painting the tubing (held along with the mandrel in a vertical orientation from the dipping fixture) with the wet brush with a bottom-to-top motion in a first pass, and then in a second pass after rotating the tubing and mandrel 90 degrees about the vertical axis of the tubing and mandrel. Once the primer has been applied to the tubing in this manner, the tubing is allowed to dry while exposed in a humidity chamber at 50%-70% relative humidity and 23°–28° C. temperature for 30-45 minutes.

Flowable silicone material is prepared using, for example, a 2-part medical silicone such as MED-4011 (Parts A and B) from NuSil Technology of Carpinteria, California USA. The silicone elastomer (Part A) and liquid crosslinker (Part B) are combined in a mix of 10 parts elastomer with 1 part crosslinker, and mixed in a sealed container in a centrifugal mixer at 3000 rpm for 60 seconds. After mixing, the silicone is allowed to sit for ten minutes before the container is unsealed.

The flowable silicone is then poured into the reservoir cylinder, and the reservoir is positioned in a programmable dipping apparatus beneath a vertically moveable dipping actuator. The dipping fixture, mandrel and tubing are mounted on the dipping actuator with the mandrel and tubing in a vertical, downward-extending orientation, and the vertical axis of the mandrel and tubing aligned with the central vertical axis of the reservoir cylinder. The dipping apparatus is then operated to lower the dipping actuator, mandrel and tubing to a position in which the lower end of the tubing is just above the surface of the silicone. The tubing and mandrel are then lowered or dipped into the silicone substantially along a straight line at a velocity of 2.29 mm per minute, over a stroke distance of 110 mm. At the bottom of the stroke, the dipping actuator, tubing and mandrel are raised out of the silicone at a velocity of 400 mm/minute.

The fixture, mandrel and coated tubing are then removed from the dipping apparatus and placed in an oven at 100° C. temperature for 15 minutes. In the oven, the tubing and mandrel are oriented vertically but inverted relative to their orientation employed during the dipping process. After removal from the oven, the coated tubing is allowed to cool for 5 minutes. After cooling, the tubing is sliced into individual proximal engagement members 182 with a series of cuts made along the tubing orthogonal to the longitudinal axis of the tubing.

In some embodiments, the proximal engagement member can have an axial length of 2.25 mm, overall outside diameter of 0.02275-0.02500", inside diameter of 0.010", inner layer 230 thickness (e.g., polyimide tubing wall thickness) of 0.0015", outer layer 232 thickness greater than 0.003", and inner layer 230 outside diameter of 0.0135" or less.

The use of a "high-grip" material such as silicone for the outer layer 232 makes practical the use of a proximal engagement member 182 that is relatively short in axial length (i.e., the dimension measured along or parallel to the longitudinal axis A-A). The proximal engagement member can be less than 5.0 mm in axial length, or less than 3.0 mm in axial length, or between 1.3 mm and 5.0 mm in axial length, or between 1.3 mm and 3.0 mm in axial length. Generally, a shorter proximal engagement member 182 is advantageous because shortness tends to reduce the tendency of the engagement member 182 to stiffen the core assembly 140 and delivery system 100. Accordingly there is made possible in some embodiments an engagement member 182 that not only can rotate about the core member 160 but can also effectively grip the inner surface of the stent 200 even at lengths below 5 mm, or below 3 mm.

Figure 10:
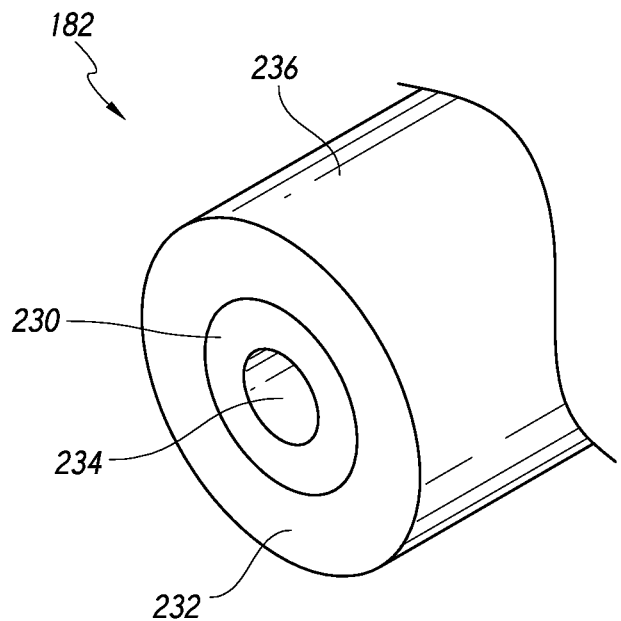
FIGS. 10 and 11 are partial perspective views of an engagement member, according to some embodiments.
Figure 11:
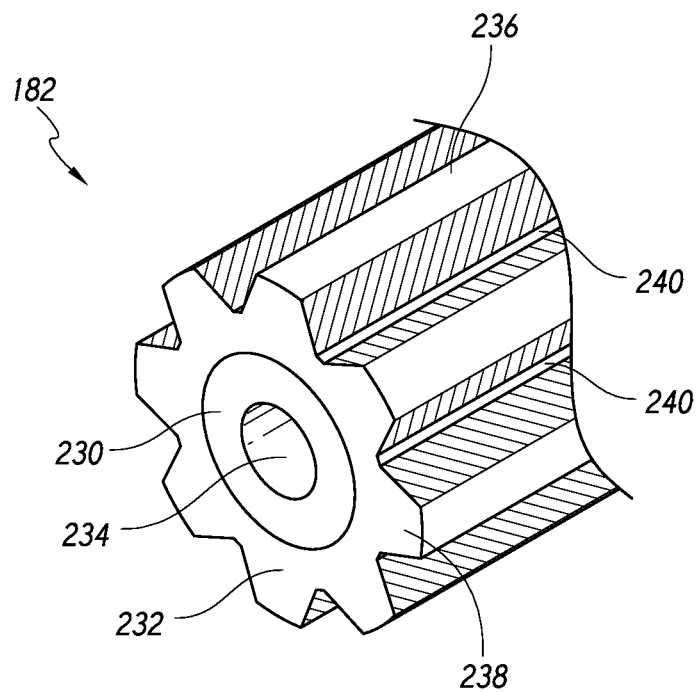

As may be observed from FIGS. 10 and 11, the outer surface 236 of the outer layer 232 can comprise a generally smooth surface as shown in FIG. 10, or a non-smooth surface such as that shown in FIG. 11, comprising, for example, a number of outwardly projecting and longitudinally extending ridges 238 that alternate with longitudinally extending recesses 240. Other patterns of projecting members and recesses, such as combinations of spikes and recessed portions, can also be employed.

Figure 12:
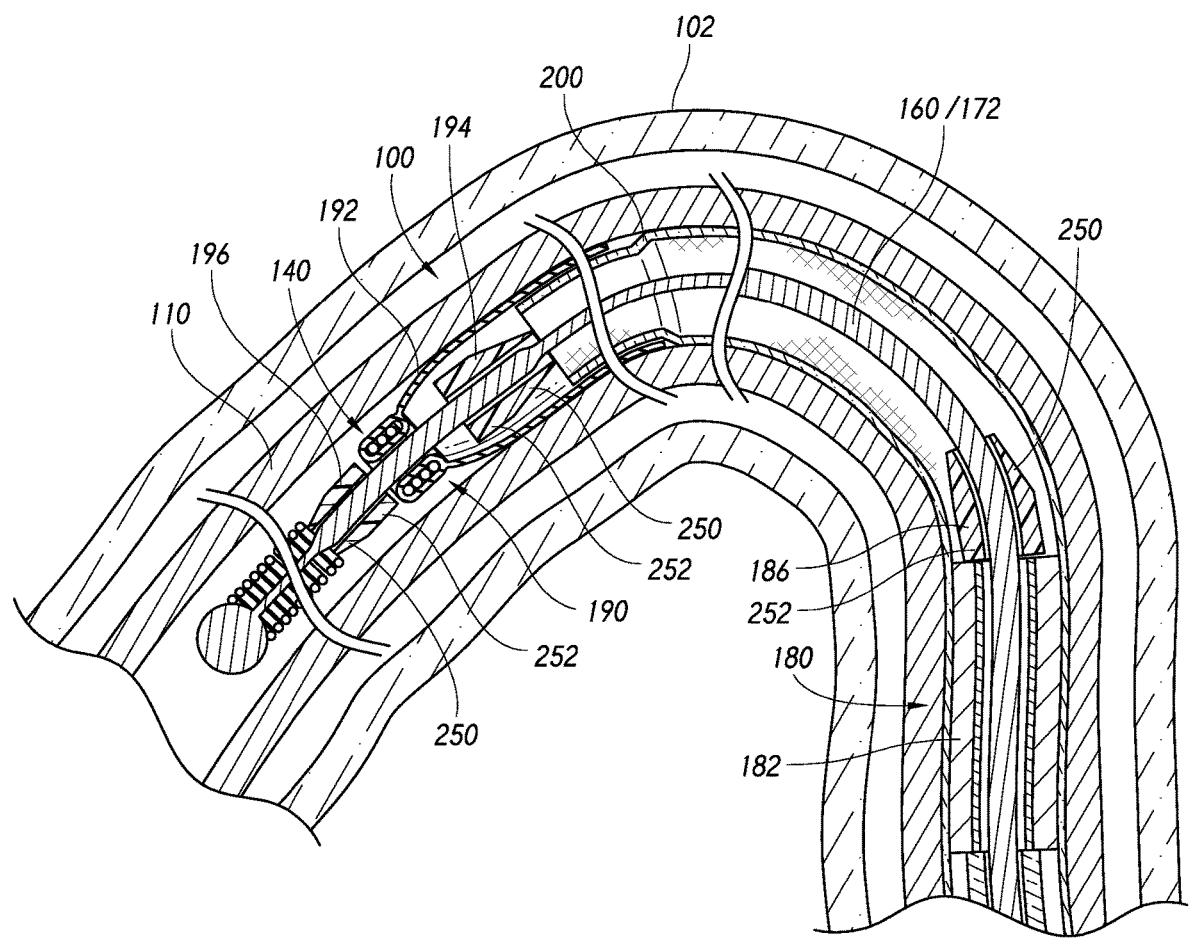
FIG. 12 is a side, cross-sectional view of a medical device delivery system being advanced through a torturous pathway, according to some embodiments.

With reference now to FIGS. 3, 4 and 12, it may be observed that the distal restraint 186 of the proximal device interface 180, and/or the proximal and/or distal restraints 194, 196 of the distal device interface 190, can each optionally comprise a tapered portion 250 and a cylindrical or non-tapered portion 252. In the proximal device interface 180, the distal restraint 186 can form a tapered portion 250 that is located distal of its non-tapered portion 252, and tapers down in diameter or cross-sectional size as it extends distally, away from the proximal engagement member 182. In the distal device interface 190, the proximal restraint 194 can form a tapered portion 250 that is located proximal of its non-tapered portion 252, and tapers down in diameter or cross-sectional size as it extends proximally, away from the distal engagement member 192; the distal restraint 196 can form a tapered portion 250 that is located distal of its non-tapered portion 252, and tapers down in diameter or cross-sectional size as it extends distally, away from the distal engagement member 192. Accordingly, in the depicted embodiment each of the restraints 186, 194, 196 forms a tapered portion 250 that tapers radially inwardly as it extends away from its respective engagement member 182/192 and/or its respective longitudinal gap (s) 187/197.

By incorporating the tapered portion(s) 250, the restraint (s) 186, 194, 196 can provide the benefit of relatively large diameter or cross-sectional size in the non-tapered portion 252 (effective longitudinal restraint of the engagement member 182/192) and/or relatively long axial length (secure attachment to the core member 160) without suffering the drawback of increased stiffness or reduced bendability of the core assembly 140 and delivery system 100. This may be understood best with reference to FIG. 12, which shows the delivery system 100 including the core assembly 140 passing through a bend in the vessel 102. In this drawing it can be observed that the tapered portion 250 of the distal restraint 186 of the proximal device interface 180 provides ample clearance for the sharply bending adjacent portion of the catheter 110 and stent 200, as compared to a non-tapered restraint of similar length and cross-sectional size or diameter. Accordingly the tapered restraint 186 allows the core assembly 140 and core member 160 to bend more sharply (and/or to bend without the restraint contacting the inner surface of the stent 200) in the vessel 102 than would be possible with a non-tapered restraint of similar axial length and cross-sectional size or diameter. In this manner the risk of a distal corner of the restraint 186 impinging on the inner surface of the stent 200 and creating a pressure concentration that can require a higher push force from the user, is reduced.

With further reference to FIG. 3, in some embodiments the distal restraint 196 of the distal device interface 190 may have a smaller (maximum) outside diameter or cross-sectional size than the proximal restraint 194 of the distal interface 190. Such a smaller distal restraint can help provide radial clearance for the everted first end 192a of the distal cover 192 during retraction into the catheter 110.

In some embodiments, one, some, or all of the restraints 184, 186, 194, 196 can comprise a tapered coil. Such coil(s) can be formed from wire stock with a tapering diameter; when wound into a coil the resulting coil tapers to a smaller diameter in the smaller diameter region of the wire. Restraints in the form of coils can provide a high degree of flexibility and improve the bendability of the core assembly 140 and delivery system 100.

One, some or all of the restraints 184, 186, 194, 196 can be formed from a radiopaque material (e.g., platinum, iridium, alloys thereof, etc.), so as to facilitate visibility of the respective portions of the core assembly 140 in a patient via fluoroscopy or other imaging. In one configuration, at least the distal restraint 186 of the proximal device interface 180 is radiopaque, and the catheter 110 is radiopaque at or near its distal tip, so as to indicate to the user that the proximal engagement member 182 is soon to exit the distal end of the catheter 110, and the delivery system 100 or core assembly 140 as a result will lose the capability to withdraw the stent 200 back into the catheter 110. Accordingly the user can observe via fluoroscopy that the distal restraint 186 is approaching the distal end 114 of the catheter 110 and thereby recognize that the delivery system 100 or core assembly 140 will soon lose the capability to withdraw the stent 200 back into the catheter 110.

As mentioned previously, the core member 160 can optionally be of multi-member construction, and can include the tube 170 which can comprise a hypotube. The tube 170 can have a sidewall that is "uncut" or without openings or voids formed therein. Alternatively, the tube 170 can have openings, voids or cuts formed in the sidewall to enhance the flexibility of the tube. This may be done by cutting a series of slots in the sidewall along part or all of the length of the tube, or cutting or drilling a pattern of other openings in the sidewall, or cutting a spiral-shaped void in the sidewall.

In some embodiments, for example where the delivery system is to be used in narrow and/or tortuous vasculature, such as the neurovasculature, the tube 170 can be of relatively small outside diameter (e.g., 0.040" or less, or 0.030" or less, or 0.027" or less, or about 0.020"); have a relatively thin sidewall thickness (e.g., 0.0050" or less, or 0.0040" or less, or about 0.0030", or between 0.0025" and 0.0035"); and/or be of relatively long overall length (e.g., 50 cm or more, or 60 cm or more, or 70 cm or more, or 80 cm or more, or about 91 cm). Instead of or in addition to any one or combination of such dimensions, the tube can have a relatively long cut length (the length of the portion of the tube in which opening(s), void(s), cut(s), spiral(s) is/are present) of 50 cm or more, or 60 cm or more, or 70 cm or more, or 80 cm or more, or about 86 cm.

A relatively long, small-diameter and/or thin-walled spiral-cut tube offers certain advantages for use in the core member 160 in narrow and/or tortuous vasculature, such as the neurovasculature. The tube can be made highly flexible (or inflexible as the case may be) where necessary by use of an appropriate spiral pitch, and the column strength or "pushability" of the tube can be maintained largely independent of its flexibility, as the diameter of the tube can remain constant along its length, in contrast with a long tapering wire which must sacrifice pushability for flexibility as it narrows. The combination of high flexibility and pushability can facilitate easier navigation into difficult, tortuous vascular locations.

Figure 13:
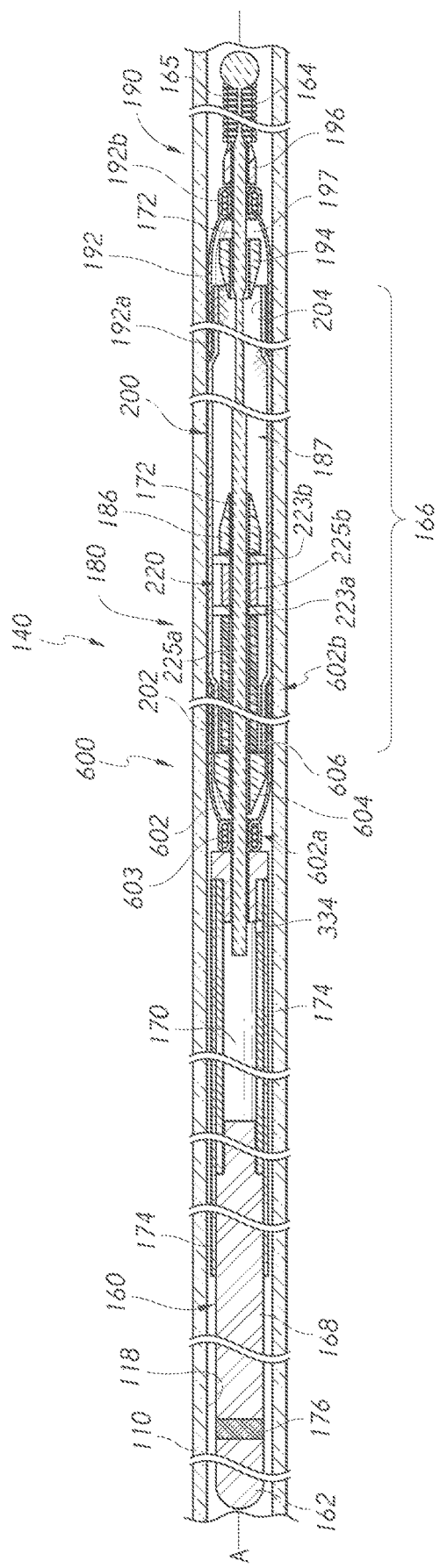
FIG. 13 is a is a side, cross-sectional view of a core assembly of the medical delivery device with a proximal cover in a first position, according to some embodiments.
Figure 14:
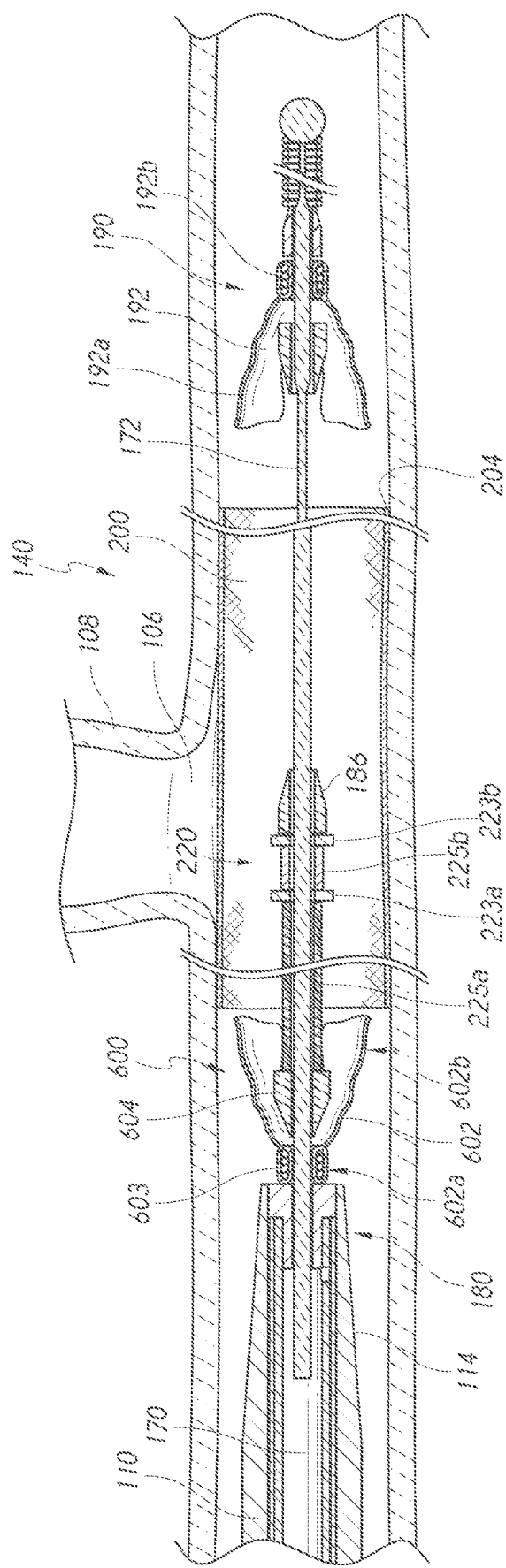
FIG. 14 is a side, cross-sectional view of the delivery system shown in FIG. 13 with the proximal cover in a second position.

As illustrated in FIGS. 13 and 14, in various embodiments the core assembly 140 can include a stent engagement assembly 220 that can interconnect the stent 200 with the core member 140. The stent engagement assembly 220 can include first and second engagement members 223a—b (together "engagement members 223") mounted over the core member 160 and/or distal wire 172 and configured to mechanically engage or interlock with the stent 200. For example, the engagement members 223 can interlock with the stent 200 by projecting into the pores thereof. In some embodiments, the engagement members 223 can additionally or alternatively engage other portions or surfaces of the stent 200 via other coupling means. In any case, the stent engagement assembly 220 cooperates with an overlying inner surface of a surrounding catheter 110 to grip the stent 200 such that the stent engagement assembly 220 can move the stent 200 along and within the catheter 110, e.g., as the user pushes the core member 160 distally and/or pulls the core member 160 proximally relative to the catheter 110, resulting in a corresponding distal and/or proximal movement of the stent 205 within the catheter lumen.

In some embodiments, each of the first and second stent engagement members 223a—b includes a central aperture configured to receive the core member 160 (such as the distal wire 172 or other components) therethrough. The opening of the aperture can be larger than the diameter of the core member 160 and/or distal wire 172 such that the engagement members 223 can rotate about the long axis of the core member 160 and/or distal wire 172. In some embodiments, the aperture can be sufficiently larger than the diameter of the core member 160 and/or distal wire 172 to permit a degree of tilting of the engagement members 223 with respect to a longitudinal axis of the core member 160 and/or distal wire 172.

The engagement members 223 can be made to have a relatively thin and/or plate-like or sprocket-like configuration. Such a configuration can facilitate the formation of projections that are small enough to fit inside the pores of the stent 200. To effectively push or pull the stent 200 along a surrounding catheter 110, the engagement members 223a—b can be made to be rigid (e.g., incompressible by the forces encountered in typical use of the delivery system). The rigidity of the engagement members 223a—b can be due to their material composition, their shape/construction, or both. In some embodiments, the engagement members 223 are made of metal (e.g., stainless steel, Nitinol, etc.) or rigid polymers (e.g., polyimide, PEEK), or both. In some embodiments, even if the engagement members 223a—b are made of a rigid material, the stent engagement members 223a—b may be non-rigid and at least partially compressible based on other structural characteristics.

In some embodiments, the core assembly 140 includes one or more spacers. For example, the core assembly 140 shown in FIGS. 13 and 14 includes a first spacer 225a and a second spacer 225b. The first spacer 225a can be positioned over the core member 160 between a portion of the core assembly 140 configured to abut a proximal end of the stent 200 (such as shoulder 604, described herein) and a proximal end of the stent engagement assembly 220. The first spacer 225a, for instance, can be positioned between a portion of the core assembly 140 configured to abut a proximal end of the stent 200 and the first stent engagement member 223a to maintain an axial position of the first stent engagement member 223a. In these and other embodiments, the second spacer 225b can be positioned over the core member 160 between the first and second stent engagement members 223a—b. The spacers 225a—b can be a substantially cylindrical body having a smaller outer diameter than the largest outer diameter of the stent engagement members 223. In some embodiments, the spacers 225a—b includes a central aperture sized and configured to allow the spacers 225a—b to be rotatably mounted over the core member 160 and/or distal wire 172. The spacers 225a— b can have end walls that are orthogonal to a long axis of the distal wire 172. These orthogonal end walls can help preserve the orthogonal orientation of the stent engagement members 223a-b relative to the distal wire 172 to prevent loss of engagement with stent 200. In some embodiments, the engagement members 223a—b can be configured to tilt to a desired degree. According to several embodiments, the spacers 225a—b can be a wire coil defining a cylindrical body mounted over the core member 160 and/or distal wire 172, for example a zero-pitch coil. In other embodiments, the spacers 225a—b can take other forms, for example a solid cylindrical tube or other element coupled to the core member 160 and/or distal wire 172. The engagement members 223a—b and the spacers 225a— b can be coupled to (e.g., mounted on) the core member 160 so that the stent engagement assembly 220 can rotate about the longitudinal axis of the core member 160 and/or move or slide longitudinally along the core member 160. In some embodiments, the core assembly 140 does not include the first spacer 225a. In some embodiments, the core assembly 140 does not include the second spacer 225b.

In some embodiments, the stent engagement assembly 220 includes a restraint 186 disposed distally to the distalmost engagement member 223b. The restraint 186 can be fixed to the core member 160 and/or wire 172 so as to be immovable relative to the core member 202, either in a longitudinal/sliding manner or a radial/rotational manner. The restraint 186 can taper in the distal direction down towards the core member 160. This tapering can reduce the risk of the restraint 186 contacting an inner surface of the overlying stent 200, particularly during navigation of tortuous vasculature, in which the system 100 can assume a highly curved configuration. In some embodiments, the restraint 186 can have an outside diameter or other radially outermost dimension that is smaller than the outside diameter or other radially outermost dimension of the overall stent engagement assembly 220, so that restraint 186 will tend not to contact the inner surface of the overlying stent 200.

In some embodiments, the stent engagement assembly 220 can be configured to engage the stent 200 within only a proximal portion (e.g., the proximal most 5%, the proximal most 10%, the proximal most 20%, only a proximal half, etc.) of the stent 200. In other embodiments, the stent engagement assembly 220 can engage the stent 200 at any location along substantially its entire length.

As illustrated in FIGS. 13 and 14, in some embodiments the core assembly 140 includes a proximal device interface 600. In FIG. 13, the stent 200 is shown in a compressed delivery state within the catheter 110. In FIG. 14, the catheter 110 has been withdrawn and the stent 200 is in a fully expanded state, positioned within the blood vessel lumen. As shown, the proximal device interface 600 can comprise a proximal cover 602 and a bumper or shoulder 604, both coupled (directly or indirectly) to the core member 160. The shoulder 604 can be positioned along the core member 160 at a location proximal of a proximal terminus of the compressed stent 200. For example, a distal face 606 of the shoulder 604 can be configured to abut a proximal terminus of the stent 200. When the stent 200 is pushed distally within the catheter 110, the shoulder 604 can transmit distal pushing force to the stent 200. The proximal cover 602 can be configured to partially or completely cover the interface between the shoulder 604 and the proximal end region of the stent 200, thereby protecting the proximal end region of the stent 200 and an inner surface of the catheter 110, as described herein.

The proximal cover 602 can comprise a flexible structure having a fixed first end portion 602a coupled (directly or indirectly) to the core member 160 and a free second end portion 602b. The proximal cover 602 can have a first position in which the second end portion 602b of the proximal cover 602 extends distally from the first end portion 602a over at least a portion of the stent 200 and/or intermediate portion 166 of the core assembly 160. In the first position, the proximal cover 602 is positioned between the stent 200 and the catheter 110. The proximal cover 602 can be movable from the first position to a second position in which the proximal cover 602 is uncoupled from the stent 200. For example, when the stent 200 is released from the constraints of the catheter 110, the expansion force of the stent 200 pushes the proximal cover 602 radially outwardly at least until an outer surface of the stent 200 is radially beyond the radially outermost portion of the proximal cover 602. A length of the proximal cover 602 can be less than an outer diameter of the stent 200 so that the proximal cover 602 does not get trapped between the stent 200 and the vessel wall. In some embodiments, a length of the proximal cover 602 is less than half of the outer diameter of the stent 200. In the uncoupled state, the proximal cover 602 can be radially and/or axially spaced apart from the stent 200. In some embodiments, the proximal cover 602 can be everted in the second position such that the first end portion 602a of the proximal cover 602 is positioned distally relative to the second end portion 602b of the proximal cover 602.

If the proximal cover 602 were absent, and therefore not positioned as in FIG. 13 between (a) the interface between the proximal end region of the stent 200 and the abutting face of the shoulder 604, and (b) the inner surface of the catheter 110, during distal advancement of the stent 200 the axially-resistive force of the stent 200 against the shoulder 604 can force all or some portions of the proximal end of the stent 200 to bend and/or flare and move radially outward of the shoulder 204 and proximal of the distal face of the shoulder 204. This is especially true when the stent 200 comprises a plurality of braided wires. The barrier provided by the proximal cover 602 combined with the compressive force of the catheter 110 prevents the proximal wire ends from bending radially outwardly and potentially penetrating the inner liner of the catheter 110 and/or breaking into smaller fragments that can cause embolic complications. The proximal cover 602 can be particularly beneficial during resheathing of the stent 200 along a curved segment. In such scenarios, the proximal end of the wires tend to remain straight. Additionally or alternatively, the proximal cover 602 can be configured to reduce friction between the medical device or stent 200 (e.g., the proximal portion or proximal end thereof) and the inner surface 118 of the catheter 110 (see FIG. 1).

The proximal cover 602 can comprise one or more flexible, generally longitudinally extending strips, wings, or elongate portions that are coupled to or integrally formed with the first end portion 602a. The proximal cover 602 can be manufactured or otherwise cut from a tube of the material selected for the proximal cover 602 or from multiple radial portions of such a tube. In some embodiments, the second end portion 602b may be formed as multiple longitudinal strips cut from the tube, and the first end portion 602a may be an uncut (or similarly cut) length of the tube. Accordingly, the first end portion 602a and the distally extending strips of the second end portion 602b may form a single, integral device or structure. In some embodiments, the proximal cover 602 comprises only one, or no more than two strips, wings, or elongate portions.

In some embodiments, the proximal cover 602 may comprise a tube or a longitudinally slit tube, and the second end portion 602b can include two or more semi-cylindrical or partially cylindrical strips or tube portions separated by a corresponding number of generally parallel, longitudinally oriented cuts or separations formed or otherwise positioned in the sidewall of the tube. Therefore, when in the pre-expansion state, as shown in FIG. 13, the second end portion 602b may generally have the shape of a longitudinally split or longitudinally slotted tube extending or interposed radially between the outer surface of the stent or device 200 and the inner surface 118 of the catheter 110.

In various embodiments, the strips, wings, or elongate portions of the second end portion 602b may collectively span substantially the entire circumference of the outer surface of the stent 200 (e.g., where the cuts between the strips are splits of substantially zero width) or be sized somewhat less than the entire circumference (e.g., where the cuts between the strips are slots having a nonzero width). In accordance with some embodiments, the width of the strips, wings, or elongate portions of the second end portion 602b can be between about 0.5 mm and about 4 mm. The width can be about 0.5 mm to about 1.5 mm. In accordance with some embodiments, the width can be about 1 mm.

The strips, wings, or elongate portions of the second end portion 602b can extend longitudinally over at least a portion of the proximal portion of the stent 200. In some embodiments, each of the strips, wings, or elongate portions of the proximal cover 602 having a length that is less than an outer diameter of the stent 200. In various embodiments, the second end portion 602b can extend between about 1 mm and about 3 mm, or between about 1.5 mm and about 2.5 mm, or about 2 mm, over the proximal portion of the stent 200.

The first end portion 602a and the second end portion 602b and can define a total length of the proximal cover 602. In some embodiments, the total length can be between about 4 mm and about 10 mm. The total length can also be between about 5.5 mm and about 8.5 mm. In some embodiments, the total length can be about 7 mm.

The strips of the second end portion 602b may be of substantially uniform size. For example, the second end portion 602b can comprise two strips spanning approximately 180 degrees each, three strips spanning approximately 120 degrees each, four strips spanning approximately 90 degrees each, or otherwise be divided to collectively cover all or part of the circumference of the stent, etc. Alternatively, the strips may differ in angular sizing and coverage area without departing from the scope of the disclosure. In one embodiment, only two strips or tube portions are employed in the second end portion 602b. The use of only two strips can facilitate radial expansion, distal movement and/or fold-over or everting of the second portion 602b, as discussed herein, while minimizing the number of free or uncontained strips in the blood vessel lumen and any potential for injuring the vessel by virtue of contact between a strip and the vessel wall. In some embodiments, a single strip is employed and can wrap around the proximal portion of the stent 200 when the proximal cover 602 is in the pre-expanded position.

The proximal cover 602 can be manufactured using a lubricious and/or hydrophilic material such as PTFE or Teflon®, but may be made from other suitable lubricious materials or lubricious polymers. The proximal cover 602 can also comprise a radiopaque material which can be blended into the main material (e.g., PTFE) to impart radiopacity. The proximal cover 602 can have a thickness of between about 0.0005" and about 0.003". In some embodiments, the distal cover can be one or more strips of PTFE having a thickness of about 0.001".

The proximal cover 602 (e.g., the first end portion 602a thereof) can be coupled to the core member 160 so that the proximal cover 602 is fixed to the core member 160 (e.g., to the proximal wire 168 or distal wire 172) so as to be immovable relative to the core member 160, either in a longitudinal/sliding manner or a radial/rotational manner. In some embodiments, the proximal cover 602 (e.g., the first end portion 602a thereof) can be coupled to (e.g., mounted on) the core member 160 so that the proximal cover 602 can rotate about the longitudinal axis A-A of the core member 160 (e.g., of the proximal wire 168 or distal wire 172), and/or move or slide longitudinally along the core member. In some embodiments, the first end portion 602a can have an inner lumen that receives the core member 160 therein such that the proximal cover 602 can slide and/or rotate relative to the core member 160.

In various embodiments, the proximal device interface 600 can comprise a radial gap between the outer surface of the core member 160 (e.g., of proximal wire 168 or the distal wire 172) and the inner surface of the first end portion 602a. Such a radial gap can be formed when the first end portion 602a is constructed with an inner luminal diameter that is somewhat larger than the outer diameter of the corresponding portion of the core member 160. When present, the radial gap allows the proximal cover 602 and/or first end portion 602a to rotate about the longitudinal axis A-A of the core member 160.

As depicted in FIG. 13, in some embodiments, the first end portion 602a of the proximal cover 602 can include an internal hoop 603. In some embodiments, the internal hoop 603 can include substantially the same components as, and function substantially similar to, the internal hoop 192c. For example, the internal hoop 603 can comprise a (metallic or polymeric) coil as depicted, or other generally rigid, tubular or cylindrical internal member such as a short segment of relatively stiff polymeric or metallic tubing, similar to the internal hoop 192c. The internal hoop 603 can be contained in an annular enclosure or loop(s) formed by first end portion 602a, or otherwise attached to or integrated into the first end portion 602a in a manner that tends to maintain an inside diameter of the proximal cover 602 in the first end portion 602a that is larger than the outside diameter of the adjacent portion of the core member 160 (or the proximal wire 168 or distal wire 172 thereof). In other words, in some embodiments, the internal hoop 603 can help maintain the presence of the radial gap between the inside diameter of the first proximal end portion 602a and the outside diameter of the core member 160, proximal wire 168, or distal wire 172.

The annular enclosure or loop(s) of the first end portion 602a can be formed by wrapping a portion of a sheet or tube of the distal cover material (e.g., PTFE) around the sidewall and through the lumen of the hoop 603 and adhering, gluing or heat bonding an end of the wrapped portion of the sheet or tube to the adjacent, distally extending portion of the sheet or tube. This positioning can form two layers that are adhered together on the distal side of the internal hoop 603. Where the proximal cover 602 material comprises PTFE, unsintered PTFE can be used to enable bonding the two portions of the material together with heat and pressure, which is not typically possible with "ordinary" or sintered PTFE.

In some embodiments, the proximal device interface 600 can comprise a bumper or shoulder 604. The shoulder 604 can be coupled to the core member 160 and located distal of the first end portion 602a of the proximal cover 602. The shoulder 604 can be coupled to the core member 160 so that the shoulder 604 is fixed to the core member 160 (e.g., to the proximal wire 168 or distal wire 172 thereof) so as to be immovable relative to the core member 160, either in a longitudinal/sliding manner or a radial/rotational manner. In some embodiments, the shoulder 604 can be coupled to (e.g., mounted on) the core member 160 so that the shoulder can rotate about the longitudinal axis A-A of the core member 160 and/or move or slide longitudinally along the core member. In some embodiments, the shoulder 604 can be configured to engage with the stent 200 to assist with adjusting the stent longitudinally. For example, a distal end portion of the shoulder 604 can abut the proximal end portion of the stent 200 so that the shoulder 604 will push the stent 200 distally when the shoulder 604 is moved distally, for example, during distal advancement of the stent 200 toward a treatment location in a patient. In some embodiments, the shoulder 604 is tapered so that the proximal end portion of the shoulder 604 has a smaller circumference than the distal end portion of the shoulder 604. In various embodiments, the proximal cover 602 is configured to surround at least a portion of the shoulder 604. For example, as depicted in FIG. 13, the proximal cover 602 extends past the shoulder 604 and encloses the shoulder 604 when the proximal cover 602 is in the first position.

In operation, the proximal cover 602, and in particular the second end portion 602b, can generally cover and protect the proximal end 202 of the stent 200 as the stent 200 is moved distally and/or proximally within the catheter 110. The proximal cover 602 may serve as a bearing or buffer layer that, for example, inhibits filament ends of the proximal end 202 of the stent 200 from contacting the inner surface 118 of the catheter 110, which could damage the stent 200 and/or catheter 110, or otherwise compromise the structural integrity of the stent 200. Since the proximal cover 602 may be made of a lubricious material, the proximal cover 602 may exhibit a low coefficient of friction that allows the proximal end 202 of the stent 200 to slide axially within the catheter 110 with relative ease. The coefficient of friction between the distal cover and the inner surface of the catheter can be between about 0.02 and about 0.4. For example, in embodiments in which the distal cover and the catheter are formed from PTFE, the coefficient of friction can be about 0.04. Such embodiments can advantageously improve the ability of the core assembly to pass through the catheter, especially in tortuous vasculature.

Further, at least a portion of the proximal cover 602 can at least partially extend or be interposed radially between the proximal portion of the stent 200 and the inner surface 118 of the catheter 110 in the first position, configuration, or orientation. In the first orientation, the second end portion 602b of the proximal cover 602 can extend from the first end portion 602a in a distal direction to a point where the second end portion 602b is interposed between the proximal portion of the stent 200 and the inner surface 118 of the catheter 110.

In this orientation, the second end portion 602b of the proximal cover 302 can take on a "distally oriented" position or configuration.

In operation, the core assembly 140 can be distally advanced until the distal portion of the stent 200 is positioned distally beyond the distal end 114 of the catheter 110 to permit expansion of the distal portion of the stent 200 into a lumen 104 of the blood vessel 102. In some embodiments, the proximal cover 602 can transition from a first position, where the second end portion 602b of the proximal cover 602 at least partially surrounds a proximal end portion of the stent 200, and a second position, where the second end portion 602b of the proximal cover 200 is uncoupled from the stent 200. Expansion of the stent 200, for example, may cause the proximal cover 602 to transition between the first and second positions. In various embodiments, the proximal cover 602 will remain in the first position if the proximal end portion of the stent 200 is positioned proximally of the distal end 114 of the catheter 110. In various embodiments, when the proximal portion of the stent 200 is positioned distally beyond the distal end 114 of the catheter 110, the stent 200 transitions from a compressed state to an expanded state. As the stent 200 transitions to the expanded state, the proximal cover 602 can transition from the first position to the second position. For example, the stent 200 expanding can cause the proximal cover 602 to uncouple from the stent 200 by pushing the free second end portion 602b of the proximal cover 602 away from the stent 200. In various embodiments, the stent 200 transitioning from the compressed state to the expanded state can cause the proximal cover 602 to evert. In some embodiments, the proximal cover 602 transitioning from the first position to the second position can cause one or more longitudinal strips of the proximal cover 602 to separate. After the proximal cover 602 has become disengaged from the stent 200, the proximal cover 602 can remain substantially in the disengaged configuration until the core assembly 140 is withdrawn proximally into the catheter 110.

Structures other than the herein-described embodiments of the proximal cover 602 may be used in the core assembly 140 and/or proximal device interface 600 to cover or otherwise interface with the proximal end 202 of the stent 200. For example, a protective coil or other sleeve having a longitudinally oriented, proximally open lumen may be employed. Suitable such protective coils include those disclosed in U.S. Patent Application Publication No. 2009/0318947 A1, published on Dec. 24, 2009, titled SYSTEM AND METHOD FOR DELIVERING AND DEPLOYING AN OCCLUDING DEVICE WITHIN A VESSEL.

In some embodiments, the stent 200 can be rotatable with respect to the core member 160 about the longitudinal axis A-A thereof, by virtue of the rotatable (connections of the) stent engagement members 223a-b and proximal cover 602. In such embodiments, the stent 200, stent engagement members 223a-b and proximal cover 602 can rotate together in this manner about the core member 160. When the stent 200 can rotate about the core member 160, the core assembly 140 can be advanced more easily through tortuous vessels as the tendency of the vessels to twist the stent 200 and/or core assembly 140 is negated by the rotation of the stent 200, stent engagement members 223a—b, and proximal cover 602 about the core member 160. In addition, the required push force or delivery force is reduced, as the user's input push force is not diverted into torsion of the stent 200 and/or core member 160. The tendency of a twisted stent 200 and/or core member to untwist suddenly or "whip" upon exiting tortuosity or deployment of the stent 200, and the tendency of a twisted stent 200 to resist expansion upon deployment, are also reduced or eliminated. Further, in some such embodiments of the core assembly 140, the user can "steer" the core assembly 140 via the tip coil 165, particularly if the coil 165 is bent at an angle in its unstressed configuration. Such a coil tip 165 can be rotated about the axis A-A relative to the stent 200, engagement member 182 and/or proximal cover 602 by rotating the distal end 162 of the core member 160. Thus, the user can point the coil tip 165 in the desired direction of travel of the core assembly 140, and upon advancement of the core assembly 140 the tip 165 will guide the core assembly 140 in the chosen direction.

As noted, embodiments of the proximal cover 602 can provide various advantages. For example, the use of the proximal cover 602 can allow the core assembly 140 to be easily urged toward the treatment site within the catheter 110 and allow for the stent 200 to be retracted within the catheter 110 without damaging the catheter 110. These benefits can advantageously reduce the delivery force required to move the core assembly 140 through the catheter 110 and prevent damage to or fracture of stent filaments. Further, a flexible cover such as the depicted proximal cover 602 can also allow the proximal portion 202 of the stent 200 to open or expand radially immediately as the proximal portion of the stent 200 exits the catheter 110. The proximal cover 602 can be easily urged away from the first or encapsulating position or configuration such that the expansion of the stent 200 is not hindered and expansion can be predictable to the clinician.

Further, where the second end portion 602b is flexible, evertible, and/or provides a minimal cross-section, the intermediate portion 166 of the core assembly 140 can be easily recaptured within the catheter 110 to facilitate resheathing. Thus, the catheter 110 can remain in place in the vasculature and the entire core assembly 140 can be withdrawn therefrom. This can enable the clinician to "telescope" one or more other stents (e.g., delivering more than one stent such that it overlaps with another stent) without having to remove the catheter 110, saving time and reducing trauma to the patient. This also enables the clinician to remove the core assembly 140 and stent 200 entirely from the catheter in the event of a failure to deploy or other evident defect in the stent 200 and insert another core assembly 140 and stent 200 through the same catheter 110, with the same time savings and reduction in trauma.

In various embodiments, the proximal device interface 600 can be used in addition with the distal device interface 190. For example, the proximal device interface 600 can employ a proximal cover 602 to surround the proximal end portion of the stent 200 while the distal device interface 190 can employ a distal cover 192 to surround the distal end portion of the stent 200.

FIGS. 1, 5-9 and 12 depict some embodiments and methods of use of the medical device delivery system 100. First, the catheter 110 can be inserted into the patient's vasculature via a percutaneous access technique or other suitable method of access. The distal end 114 of the catheter 110 is then advanced to a treatment site or location in the blood vessel 102, using for example any of the access routes 400. The blood vessel 102 may comprise a vein or artery, such as an artery in a brain or within a cranium of the patient. As previously mentioned, the catheter 110 can comprise a microcatheter. A guide catheter (not shown) can be used instead of or in addition to the catheter 110; for example, the guide catheter can first be placed in the vasculature so that it extends part or all of the way to the treatment site and a microcatheter or other catheter then inserted through the guide catheter to the treatment site.

The treatment location may be near the aneurysm 108 formed in a wall of the blood vessel 102, and advancing the catheter 110 to the treatment location may include advancing the distal end 114 and/or distal opening 120 to a location that is distal of the aneurysm 108 (e.g., FIG. 5). Such advancement of the catheter 110 may include advancing the distal end 114 and/or distal opening 120 distally across the ostium or neck 106 of the aneurysm 108, to the location in the vessel 102 distal of the aneurysm.

Once the catheter 110 has been inserted, it may extend proximally from the distal end 114 and/or distal opening 120 at the treatment location, through the vascular access site, to the proximal end 112 and/or hub 122 which are preferably situated outside the patient's body.

After the catheter 110 has been placed, the core assembly 140 (with the stent 200 carried thereby) can be inserted, distal end first, into the lumen 116 of the catheter 110 via the hub 122 and/or proximal end 112. Where the core assembly 140 is initially at least partially contained within an introducer sheath the distal end of the introducer sheath can be inserted into the proximal end of the catheter 110 and the core assembly 140 is advanced distally through the introducer sheath until the distal core assembly and stent 200 exit the distal end of the introducer sheath and pass into the lumen 116 of the catheter 110. Such advancement of the core assembly 140 can comprise gripping the core member 160 in a proximal grip region as a result of its exposure proximal of the proximal end of the sheath (and/or of the sheath preventing the gripping of any other portion of the core assembly 140). When the core assembly 140 and stent have been sufficiently advanced, the introducer sheath can be retracted from the proximal end of the catheter 110 and/or discarded. Once the sheath has been so retracted/discarded, the proximal grip region can be exposed for gripping proximal of the catheter proximal end 112, and the region can be the only portion of the core assembly available for gripping by the user.

The core assembly 140 and stent 200 are at this point disposed in the catheter 110 generally as depicted in FIG. 1. In particular, the stent 200 and distal portion of the core assembly 140 can be positioned in the lumen 116 of the catheter 110, with the stent 200 generally in contact with the inner surface 118 of the catheter 110 except where the first section 192a of the distal cover 192 is extending or interposed radially between the distal end 204 of the stent 200 and the inner surface 118 of the catheter 110. Further, the core member 160 can extend proximally of the proximal end 112 and/or hub 122 of the catheter 110 to a location outside of the patient's body, so that the proximal portions (e.g., proximal wire 168 where employed, and/or the proximal grip region) of the core member 160 can be easily accessed.

Next, the core assembly 140 with the stent 200 can be axially advanced distally within the lumen 116 of the catheter 110, toward the distal end 114 of the catheter 110 and treatment location. Where the core assembly 140 includes a proximal engagement member 182, stent engagement members 223a—b, a proximal cover 602, and/or a distal cover 192 that can rotate about the core member 160, advancing the core assembly (in this method or in any method of advancing the core member 140 through a tortuous catheter, such as when such catheter is disposed in a laboratory model of vasculature) can further comprise rotating the stent 200, engagement member 182, stent engagement members 223a—b, proximal cover 602 and/or distal cover 192 about the core member 160. This can optionally be done without significant twisting of the core member 160 and/or stent 200.

Where the core assembly 140 includes one or more restraints 184, 194 and/or 196 having a tapered portion 250 (see FIG. 12), advancing the core assembly 140 (in this method or in any method of advancing the core member 140 through a tortuous catheter) can further comprise bending the core assembly 140 and core member 160 more sharply (and/or without the restraint 184, 194 and/or 196 contacting the inner surface of the stent 200) in the vessel 102 than would be possible with a non-tapered restraint 184, 194 and/or 196 of similar axial length and cross-sectional size or diameter.

Where the core assembly 140 comprises a proximal device interface 180, stent engagement member 223a—b and/or engagement member 182 positioned in a distal portion or half of the stent 200, advancing the core assembly 140 (in this method or in any method of advancing the core member 140 through a tortuous catheter) can further comprise pulling the stent 200, or the proximal portions or proximal half thereof through the catheter 110 with the interface 180, stent engagement members 223a—b, and/or engagement member 182. This can optionally further comprise exerting less push force on the core member 160 than would be required in a similar delivery system that lacks a proximal device interface 180, stent engagement members 223a—b, and/or engagement member 182 positioned in a distal portion or half of the stent 200. Furthermore, if such a core assembly 140 comprises a retraction-only interface in a proximal portion or half of the stent 200, advancing the core assembly 140 can comprise doing so with the retraction-only interface disengaged from the stent 200.

As the stent 200, proximal cover 600, and distal cover 192 are advanced toward the distal end 114 and treatment location, the second end portion 602b of the proximal cover 602 remains extending or interposed radially between the outer surface and/or proximal end 202 of the stent 200 and the inner surface 118 of the catheter 110 and the first section 192a of the distal cover 192 remains extending or interposed radially between the outer surface and/or distal end 204 of the stent 200 and the inner surface 118 of the catheter 110. Thus, the proximal cover 602 and the distal cover 192 may inhibit the proximal end and the distal end 204 of the advancing stent 200 (e.g., the filament ends thereof) from damaging, abrading, or gouging the catheter 110, and from thereby impeding progress of the stent 200 along the catheter 110. This may, in turn, avoid damage to the stent 200 such as by longitudinal compression resulting from high friction generated between the proximal end 202 and the distal end 204 of the stent 200 and the catheter 110 while distally directed force is applied to the proximal portions of the stent 200.

Where the treatment location is near the aneurysm 108 and the distal end 114 and/or distal opening 120 of the catheter 110 has been advanced to a location that is distal of the aneurysm, advancement of the core assembly 140 with the stent 200 toward the distal end 114 and treatment location can include advancing the distal portion of the core assembly 140 and the distal end 204 of the stent 200 distally through the catheter 110 across the ostium or neck 106 of the aneurysm, to a location in the vessel 102 distal of the aneurysm.

As the stent 200 moves closer to the distal end of the catheter 110, the user can observe the fluorosafe marker 176 (when present) approaching the proximal end of the catheter and thereby recognize that the stent is or will soon be close to exiting the distal end of the catheter. Having recognized this, the user can activate fluoroscopic imaging to view the exit of the stent from the distal catheter end via such imaging, and then proceed to urge the core assembly distally and thereby cause the stent to exit the distal end of the catheter.

To begin expansion of the stent 200 (see FIGS. 5-9), the core assembly 140 may be held stationary and the catheter 110 may be withdrawn proximally over the stent 200 and distal portion of the core assembly 140, as shown in FIGS. 6-7. (Optionally, the core assembly 140 and stent 200 can be advanced distally while performing this step, instead of or in addition to withdrawal of the catheter.) In any event, as a result, the stent 200 (except for any portion retained within the catheter 110) can be released and permitted to expand into engagement with the inner wall of the blood vessel 102, as shown in FIGS. 6-7. Some embodiments of the stent 200 (such as certain braided stents) can shorten axially while expanding radially. As a result of (i) any axial foreshortening of the stent 200, (ii) radial expansion of the stent 200, and/or (iii) radial expansion of the distal cover 192 in response to radial expansion of the stent 200, the strips or tube portions of the first section 192a of the distal cover 192 can disengage from contact with the distal end 204 of the stent 200, while in some embodiments separating and moving radially outward as well.

As the distal portion of the stent 200 expands, it can cause the distal cover 192 to be opened or moved from the first orientation. When the stent 200 can foreshorten as it expands, the stent 200 can withdraw from engagement with the distal cover 192, as shown in FIG. 6. After the distal cover 192 has become disengaged from the stent 200 to reach the state shown in FIG. 6, the cover can proceed to the second orientation as shown in FIG. 7, as oncoming blood flow and/or other forces urge the first section 192a distally. Alternatively, the distal cover 192 can remain substantially in the disengaged, proximally-extending configuration shown in FIG. 6 until the core assembly 140 is withdrawn proximally into the catheter 110, at which point the distal end 114 of the catheter 110 can force the approaching first section 192a of the cover 192 to evert or otherwise take on the second configuration as shown in FIGS. 7-8.

In some embodiments, as the distal cover 192 disengages from the stent 200, it no longer covers the distal end 204 of the stent 200; instead, its first section 192a is now spaced distally from the stent distal end 204 as shown in FIG. 6. In this state, the strips or tube portions forming the first section 192a can be free or unconfined within the lumen of the blood vessel 102. As similarly noted above, the strips or tube portions can have free first ends, as well as second ends that are coupled to the core assembly 140. The free first ends can cover at least a portion of the stent distal portion during delivery of the stent. Further, when the stent is expanded and/or the core assembly 140 is proximally withdrawn into the catheter, the strips or tube portions can be everted, such that free first ends of the strips, wings, or elongate portions are drawn together distal to the second ends thereof.

In some embodiments, as the proximal cover 602 disengages from the stent 200, it no longer covers the proximal end 202 of the stent 200. For example, the second end portion 602b can be spaced apart distally or proximally from the proximal end 202 of the stent. In some embodiments, the strips or tube portions forming the second end portion 602b can be free or unconfined within the lumen of the blood vessel 102. Further, when the stent 200 is expanded and/or the core assembly 140 is proximally withdrawn into the catheter, the strips or tube portions can be everted, such that free first ends of the strips, wings, or elongate portions are drawn together distal to the second ends thereof.

The pullback of the catheter 110 (and/or distal movement of the core assembly 140) and expansion of the stent 200 may be done in multiple discrete steps. For example, the catheter 110 may initially be pulled back proximally only part of the way as shown in FIGS. 6-17, and only the distal portion 204 of the stent 200 expanded into engagement with the vessel wall. Such initial partial expansion facilitates anchoring the distal portion of the stent in the vessel 102, which in turn facilitates longitudinal stretching or compression of the stent 200 as desired by the clinician during or prior to expansion of the remaining portions of the stent 200 into the vessel 102. Initial partial expansion can also facilitate confirmation by the clinician that the distal portion of the stent 200 has "landed" in the desired location in the vessel 102 (e.g., distal of the neck or ostium of any aneurysm formed in the vessel wall) prior to expansion of the remaining portions of the stent 200. Generally, where an aneurysm is present in the vessel 102, proper placement of the stent 200 can include positioning a distal portion of the stent 200 in the vessel lumen distal of the aneurysm neck 106 and a proximal portion of the stent in the vessel lumen proximal of the aneurysm neck 106, such that the stent 200 extends across the neck (FIG. 9). Where the expanded stent 200 is appropriately configured, it may then perform a therapeutic flow-diverting function with respect to the aneurysm 108.

While the delivery system 100 is in the configuration shown in FIG. 6 or 7, with the proximal end 202 of the stent 200 retained within the catheter 110 between the proximal engagement member 182, stent engagement members 223a-b, and/or the inner wall 118 of the catheter, the partially expanded stent 200 can be resheathed or retracted proximally into the catheter 110 as shown in FIG. 8. The engagement member 182, stent engagement members 223a-b, and/or catheter 110 can secure, grip, or engage the stent 200 to a sufficient degree to permit the catheter 110 to be advanced distally over the partially expanded stent 200 (and/or the core member 160 withdrawn proximally relative to the catheter 110) until the stent 200 is again positioned in the lumen 116 of the catheter 110. Thus, the engagement member 182 and/or stent engagement members 223a-b can exert a proximal force on the stent 200 as the stent 200 is withdrawn or retracted into the catheter 110. Where the core assembly includes a retraction-only interface in a proximal half or portion of the stent, the retraction-only interface can be activated and employed to retract the stent proximally into the catheter 110. Thus, the retraction-only interface can exert a proximal force on the stent 200 as the stent 200 is withdrawn or retracted into the catheter 110.

FIGS. 6-7 also show a first aspect of a process of resheathing the stent 200, during or prior to the stent 204 being drawn into the lumen 116 of the catheter 110. Because the previously stent-engaging portion (e.g., the first section 192a) of the distal cover 192 has moved radially outward from the core member 160 (e.g., FIG. 6) and/or distally relative to the core member 160 (e.g., FIG. 7), it does not impede the entrance of the distal portion and distal end 204 of the stent 200 into the distal opening 120 of the catheter 110 (e.g., to get to the state shown in FIG. 8) during resheathing. Accordingly, the resheathing process can comprise moving the stent 200 (including the distal end 204) into the catheter 110 through the distal opening 120 while the previously stent-engaging portion (e.g., the first section 192a) of the distal cover 192 is in a second, everted, or resheathing configuration in which the stent-engaging portion is disposed radially outward from the core member 160 and/or the first section 192a of the distal cover 192 is disposed distally relative to the core member 160, the second section 192b, and/or the distal tip 165, in comparison to a first, encapsulating, or delivery configuration (e.g., FIG. 1, 3) of the stent-engaging portion (e.g., the first section 192a) of the distal cover 192.

FIG. 8 shows a second aspect of the resheathing process currently under discussion.

In this aspect of the process, the core assembly 140 can be moved further proximally into the catheter 110 (and/or the catheter 110 is moved further distally over the core assembly 140) until the distal cover 192 enters the catheter 110 via the distal opening 120. As noted above, the first section 192a of the distal cover 192 is preferably sufficiently flexible to evert and thereby attain the second, everted, or resheathing configuration shown in FIGS. 7-8. In the second, everted, or resheathing configuration, the first section 192a of the distal cover 192 can extend generally in a distal direction, away from the stent 200, and/or extend distally of the second section 192b of the distal cover 192. Further, in some embodiments, the first section 192a of the distal cover 192 can also radially overlap the distal tip 165 and/or the distal restraint 196. Instead of or in addition to these aspects of the second, everted, or resheathing configuration, the distal cover 192 can be radially small enough to extend into the lumen 116 of the catheter 110, either partially or wholly as shown in FIG. 8, and/or the entire distal cover 192 can be spaced distally from the distal end 204 of the stent 200 in the lumen 116 of the catheter 110.

Accordingly, in accordance with some embodiments of methods disclosed herein, when operating the delivery system 100, a clinician can check the initial partial expansion of the stent 200 (e.g., as shown in FIGS. 6-7) and, if the initial placement is unsatisfactory or if the initial expansion of the stent 200 is unsatisfactory, the clinician can recapture, collapse, withdraw, or resheath the stent 200 into the catheter 110, as described above with respect to FIGS. 6-8. After resheathing, the clinician can attempt to deploy the stent again, as described herein, beginning for example with the state depicted in FIG. 8, and resulting for example, in the state depicted in FIG. 6-7 or 9. Resheathing can also be performed, and the delivery system 100 and stent 200 removed from the patient entirely, if for example, the delivery and/or expansion of the stent 200 damages or reveals a defect in, or improper sizing of, the stent 200 or delivery system 100. After an initial partial expansion of the stent 200, the depicted core assembly 140 can optionally be entirely removed with the stent 200 from the catheter 110 without need to remove the catheter 110 from the blood vessel 102. In this manner, access to the treatment site in the blood vessel 102 can be maintained via the catheter 110 and, if desired, additional attempts to deliver the stent 200 can be made through the catheter 110.

If the initial expansion of the stent 200 in the vessel 102 is satisfactory, full deployment and expansion can be completed to result in the state depicted in FIG. 9. The proximal end 202 of the stent 200 may be released from the catheter 110 by holding the core member 160 stationary and withdrawing the catheter proximally relative to the core member 160 and the stent 200 until the distal opening 120 is proximal of the proximal end 202 of the stent 200. No longer constrained by the catheter 110, the proximal end 202 of the stent 200 can now expand into contact with the wall of the vessel 102, as shown FIG. 9. (Note that until this point, according to an aspect of some embodiments, the partially expanded stent 200 had been fully resheathable.) The fully deployed stent 200 extends across the neck 106 of the aneurysm 108, and can optionally perform a therapeutic flow-diverting function with respect to the aneurysm.

Following full expansion of the stent 200, the core assembly 140 can be drawn back into the catheter 110. Both the catheter 110 and core assembly 140 can be withdrawn from the patient, either simultaneously or sequentially. However, when the stent has been successfully released, the core assembly 140 can also be entirely removed from the catheter 110, with the catheter 110 remaining in place, and a second core assembly can be inserted into the catheter lumen. The second core assembly can be configured to deliver a second stent to the treatment site in order to perform, e.g., a telescoping procedure.

In the present disclosure, numerous references are made to moving the catheter 110 axially over the core assembly 140 and moving the core assembly 140 axially within the catheter 110. Except where specifically noted to the contrary, all such references to one form of this relative movement should be understood to include the other as an alternative.

Information regarding additional embodiments of the medical device delivery system 100, and additional details, components and methods that can optionally be used or implemented in or with the embodiments of the delivery system 100 described herein, can be found in U.S. patent application Ser. No. 13/664,547, filed on Oct. 31, 2012, titled METHODS AND APPARATUS FOR LUMINAL STENTING, the entirety of which is hereby incorporated by reference herein and made a part of this specification. The delivery system 100 and methods disclosed herein can optionally be similar to any of the delivery systems or methods disclosed in the above-incorporated application, except as further described herein.

The apparatus and methods discussed herein are not limited to the deployment and use of a medical device or stent within the vascular system but may include any number of further treatment applications. Other treatment sites may include areas or regions of the body including any hollow anatomical structures.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

The invention claimed is:

1. A system for delivering a stent through a catheter, the stent having a compressed state in which the stent has a first diameter and an expanded state in which the stent has a second diameter greater than the first diameter, the system comprising:
   a core member having a distal portion, wherein the distal portion is configured to be positioned within a lumen of the stent;
   an eversible cover having a first end portion coupled to the distal portion of the core member and a free second end portion, the cover having a first position in which the first end portion is proximal to the second end portion, and a second position in which the first end portion is distal to the second end portion; and
   a shoulder coupled to the distal portion of the core member at a location distal to the first end portion of the cover, the shoulder configured to abut a proximal end portion of the stent when the stent is in the compressed state and positioned over the core member within the catheter,
   wherein,
   when at least a portion of the stent is positioned in the compressed state within the catheter, the cover is in the first position in which the second end portion of the cover is interposed radially between a proximal end region of the stent and an inner surface of the catheter, and
   when the catheter is proximal of the first end portion of the cover, the cover transitions from the first position to the second position in which the second end portion is decoupled from the stent, in response to the stent transitioning from the compressed state to the expanded state and thereby pushing the cover radially outward.

2. The system of claim 1, wherein, when the cover is in the first position, the cover is interposed radially between (a) a length of the system within the catheter spanning a distal end region of the shoulder to the proximal end region of the stent, and (b) the inner surface of the catheter.

3. The system of claim 1, wherein the cover comprises one or more longitudinal strips.

4. The system of claim 3, wherein the one or more longitudinal strips are configured to wrap around the proximal end portion of the stent when the cover is in the first position.

5. The system of claim 1, wherein the cover at least partially surrounds the shoulder.

6. The system of claim 1, wherein the shoulder has a distal face configured to push the stent distally.

7. The system of claim 1, wherein the shoulder is spaced apart from the first end portion of the cover.

8. The system of claim 1, wherein a length of the cover extending between an attachment point where the first end portion is coupled to the core member and a distal edge of the second end portion is less than the second diameter.

9. The system of claim 1, wherein a length of the cover extending between an attachment point where the first end portion is coupled to the core member and a distal edge of the second end portion is less than half of the second diameter.

10. The system of claim 1, wherein the cover is a first cover, the system further comprising a second cover, the second cover having a first end coupled to the distal portion of the core member and a second end configured to at least partially surround a distal end of the stent.

11. A delivery system for delivering a stent, the stent having a compressed state in which the stent has a first diameter and an expanded state in which the stent has a second diameter greater than the first diameter, the system comprising:
    a catheter;
    a manipulation member having a distal region and configured to be slidably received within a lumen of the catheter;
    an eversible cover having a first portion coupled to the distal region of the manipulation member and a free second portion, the cover having (a) a first position in which the first portion is proximal to the second portion and the second portion is configured to at least partially surround a proximal portion of the stent while the stent is compressed within the catheter, and (b) a second position in which the first portion is distal to the second portion and the second portion is decoupled from the stent, wherein the cover transitions from the first position to the second position in response to the stent transitioning from the compressed state to the expanded state and thereby pushing the cover radially outward; and a shoulder member coupled to the distal region of the manipulation member, the shoulder member configured to abut a proximal terminus of the stent when the stent is compressed within the catheter.

12. The system of claim 11, wherein, when the cover is in the first position, the cover is interposed radially between (a) a length of the system within the catheter spanning a distal end region of the shoulder to the proximal terminus of the stent, and (b) an inner surface of the catheter.

13. The system of claim 11, wherein the cover comprises one or more longitudinal strips.

14. The system of claim 13, wherein the one or more longitudinal strips are configured to wrap around the proximal portion of the stent when the cover is in the first position.

15. The system of claim 11, wherein the cover at least partially surrounds the shoulder member.

16. The system of claim 11, wherein the shoulder member has a distal face configured to push the stent distally.

17. The system of claim 11, wherein the shoulder member is spaced apart from the first portion of the cover.

18. The system of claim 11, wherein a length of the cover extending between an attachment point where the first portion is coupled to the core member and a distal edge of the second portion is less than the second diameter.

19. The system of claim 11, wherein a length of the cover extending between an attachment point where the first portion is coupled to the core member and a distal edge of the second portion is less than half of the second diameter.

20. The system of claim 11, wherein the cover is a first cover, the delivery system further comprising a second cover, the second cover having a first portion coupled to the distal region of the manipulation member and a second portion configured to at least partially surround a distal end of the stent.

* * * * *